(12) United States Patent
Tumlinson et al.

(10) Patent No.: US 12,201,365 B2
(45) Date of Patent: Jan. 21, 2025

(54) ALIGNMENT IMPROVEMENTS FOR OPHTHALMIC DIAGNOSTIC SYSTEMS

(71) Applicants: Carl Zeiss Meditec, Inc., Dublin, CA (US); Carl Zeiss Meditec AG, Jena (DE)

(72) Inventors: Alexandre R. Tumlinson, San Leandro, CA (US); Keith O'Hara, Pleasanton, CA (US); Angelo Rago, Lafayette, CA (US)

(73) Assignees: Carl Zeiss Meditec, Inc., Dublin, CA (US); Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/141,140

(22) Filed: Apr. 28, 2023

(65) Prior Publication Data
US 2023/0255480 A1   Aug. 17, 2023

Related U.S. Application Data

(60) Continuation of application No. 17/082,714, filed on Oct. 28, 2020, now Pat. No. 11,672,421, which is a
(Continued)

(51) Int. Cl.
*A61B 3/15* (2006.01)
*A61B 3/10* (2006.01)
(Continued)

(52) U.S. Cl.
CPC .............. *A61B 3/152* (2013.01); *A61B 3/102* (2013.01); *A61B 3/1025* (2013.01); *A61B 3/12* (2013.01); *A61B 5/7415* (2013.01)

(58) Field of Classification Search
CPC ..... A61B 3/152; A61B 3/1025; A61B 5/7415; A61B 3/102; A61B 3/12
See application file for complete search history.

(56) References Cited

U.S. PATENT DOCUMENTS 2,780,956 A   2/1957   Fuller et al.
3,787,112 A   1/1974   Lyons
(Continued)

FOREIGN PATENT DOCUMENTS

EP   1369078   7/2012
GB   2451441   2/2009
(Continued)

OTHER PUBLICATIONS

Acosta et al., "Wavefront Coding Implementation for Retinal Imaging Systems", Investigative Ophthalmology & Visual Science, vol. 55, Apr. 2014, 2 pages.
(Continued)

*Primary Examiner* — Cara E Rakowski
(74) *Attorney, Agent, or Firm* — Snell & Wilmer L.L.P.

(57) ABSTRACT

The present application describes the addition of various feedback mechanisms including visual and audio feedback mechanisms to an ophthalmic diagnostic device to assist a subject to self-align to the device. The device may use the visual and non-visual feedback mechanisms independently or in combination with one another. The device may provide a means for a subject to provide feedback to the device to confirm that an alignment condition has been met. Alternatively, the device may have a means for sensing when acceptable alignment has been achieved. The device may capture diagnostic information during the alignment process or may capture after the alignment condition has been met.

15 Claims, 13 Drawing Sheets

Related U.S. Application Data division of application No. 15/749,723, filed as application No. PCT/EP2016/069098 on Aug. 11, 2016, now Pat. No. 10,849,498.

(60) Provisional application No. 62/204,317, filed on Aug. 12, 2015.

(51) Int. Cl.
  *A61B 3/12* (2006.01)
  *A61B 5/00* (2006.01)

(56) References Cited

U.S. PATENT DOCUMENTS

| | | | |
|---|---|---|---|
| 4,732,466 | A | 3/1988 | Humphrey |
| 5,313,711 | A | 5/1994 | Kling, III et al. |
| 5,474,548 | A | 12/1995 | Knopp et al. |
| 5,526,582 | A | 6/1996 | Nower et al. |
| 5,572,266 | A | 11/1996 | Ohtsuka |
| 5,909,268 | A | 6/1999 | Isogai et al. |
| 6,409,341 | B1 | 6/2002 | Goldfain et al. |
| 7,160,288 | B2 | 1/2007 | Sumiya |
| 7,252,661 | B2 | 8/2007 | Nguyen et al. |
| 7,331,670 | B2 | 2/2008 | Ichikawa |
| 7,364,295 | B2 | 4/2008 | Tawada |
| 7,445,336 | B2 | 11/2008 | Ichikawa |
| 7,458,685 | B2 | 12/2008 | Liang et al. |
| 7,641,340 | B2 | 1/2010 | Ichikawa |
| 8,025,403 | B2 | 9/2011 | Maloca et al. |
| 8,333,474 | B2 | 12/2012 | Michaels et al. |
| 8,348,429 | B2 | 1/2013 | Walsh et al. |
| 9,060,718 | B2 | 6/2015 | Lawson et al. |
| 9,237,847 | B2 | 1/2016 | Wang et al. |
| 2002/0093645 | A1 | 7/2002 | Heacock |
| 2007/0030450 | A1 | 2/2007 | Liang et al. |
| 2008/0212029 | A1* | 9/2008 | Ichikawa ............ A61B 3/12 351/208 |
| 2011/0021318 | A1 | 1/2011 | Lumsden et al. |
| 2012/0200824 | A1 | 8/2012 | Satake |
| 2012/0257166 | A1 | 10/2012 | Francis et al. |
| 2013/0194548 | A1 | 8/2013 | Francis et al. |
| 2013/0208241 | A1 | 8/2013 | Lawson et al. |
| 2014/0055745 | A1 | 2/2014 | Sato et al. |
| 2016/0128566 | A1 | 5/2016 | Durr et al. |
| 2016/0267319 | A1 | 9/2016 | Murillo et al. |

FOREIGN PATENT DOCUMENTS

| | | |
|---|---|---|
| WO | 1999/21472 | 5/1999 |
| WO | 2014/127134 | 8/2014 |
| WO | 2014/158263 | 10/2014 |

OTHER PUBLICATIONS

Benward et al., "Music: In Theory and Practice", vol. 1, McGraw-Hill College, 7 Edition, 2003, p. 67 and 359.

Dehoog et al., "Fundus Camera Systems: A Comparative Analysis", Applied Optics, vol. 48, No. 2, Jan. 10, 2009, pp. 221-228.

Hayes, Tim, "EyeSelfie gives Patients Control Over Retinal Imaging", Optics.Org, Jul. 8, 2015, pp. 1-4.

International Preliminary Report on Patentability received for PCT Patent Application No. PCT/EP2016/069098, mailed on Feb. 22, 2018, 12 pages.

International Search Report and Written Opinion received for PCT Patent Application No. PCT/EP2016/069098, mailed on Jan. 19, 2017, 16 pages.

Lawson et al., "Computational Retinal Imaging via Binocular Coupling and Indirect Illumination", Proceeding SIGGRAPH 2012, Aug. 5-9, 2012, 1 page.

Middlebrooks et al., "Sound Localization by Human Listeners", Annual Review of Psychology, vol. 42, Feb. 1991, pp. 135-159.

"Nidek AFC-230 Non-Mydriatic: Simply brilliant", Get Oct, Available at <http:/ /blog.getoct.ch/?p=142>, May 14, 2010, pp. 1-6.

"Rice MobileVision Device Lets Patients Image Their Own Retinas (Video)", Medgadget, Available at <www.medgadget.com/2015/03/rice-mobilevision-device-lets-patients-image-their-own-retinas-video.html>, Mar. 24, 2015, pp. 1-3.

Ro Staff, "Diagnostic Equipment: Entry-Level SD-OCT Model", Review of Optometry, Available at <https:/ /www.reviewofoptometry.com/article/rol014-product-review>, Oct. 15, 2014, pp. 1-4.

Samaniego et al., "MobileVision: A Face-Mounted, Voice-Activated, Non-Mydriatic "Lucky" Ophthalmoscope", Proceedings of Wireless Health, Oct. 29-31, 2014, 8 pages.

Samaniego et al., "Towards a Patient-Operable, at-Home, Non-Mydriatic Retinal Imaging System", Journal of Vision, vol. 13, No. 15, Dec. 2013, 2 pages.

Swedish et al., "EyeSelfie: Self Directed Eye Alignment using Reciprocal Eye Box Imaging", ACM Transactions on Graphics (TOG)—Proceedings of ACM SIGGRAPH 2015, vol. 34 No. 4, Aug. 2015, 11 pages.

Williams, Mike, "Minimal Device Maximizes Macula Imaging", Rice University News & Media, Available at <http://news. rice. ed u/2015/03/18/m in i ma Idevicem axi m izesm acu la i magi ng2/>, Mar. 18, 2015, pp. 1-3.

Winckel, Fritz, "Simultaneously Sounding Tones", Chapter VIII, Music, Sound and Sensation: A Modern Exposition, 1967, p. 134.

USPTO, Notice of Allowance dated Jul. 29, 2020 with U.S. Appl. No. 15/794,723.

USPTO, Restriction Requirement dated Nov. 5, 2019 with U.S. Appl. No. 15/794,723.

USPTO, Non Final Office Action dated Jan. 17, 2020 with U.S. Appl. No. 15/794,723.

USPTO, Non Final Office Action dated Oct. 28, 2022 with U.S. Appl. No. 17/082,714.

USPTO, Notice of Allowance dated Feb. 7, 2023 with U.S. Appl. No. 17/082,714.

USPTO, Corrected Notice of Allowability dated Feb. 15, 2023 with U.S. Appl. No. 17/082,714.

\* cited by examiner

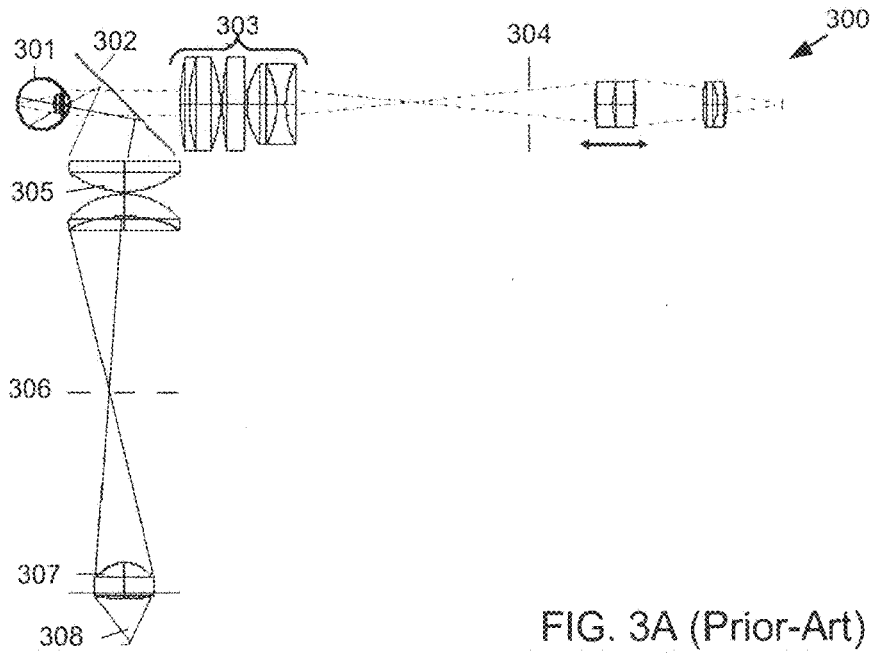
FIG. 3A (Prior-Art)
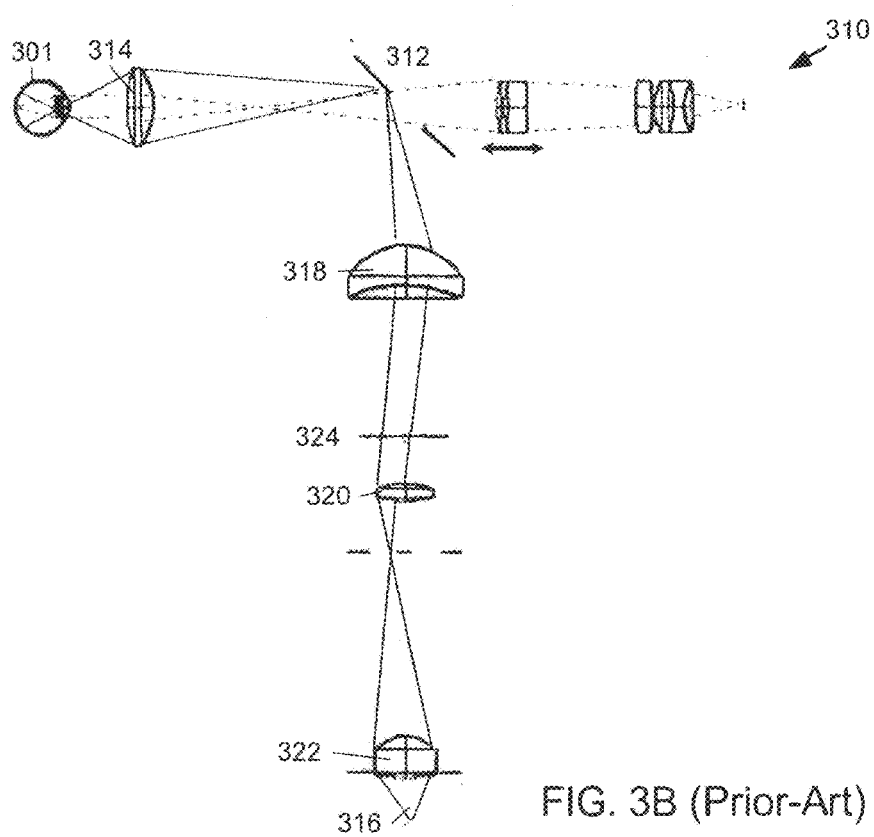
FIG. 3B (Prior-Art)

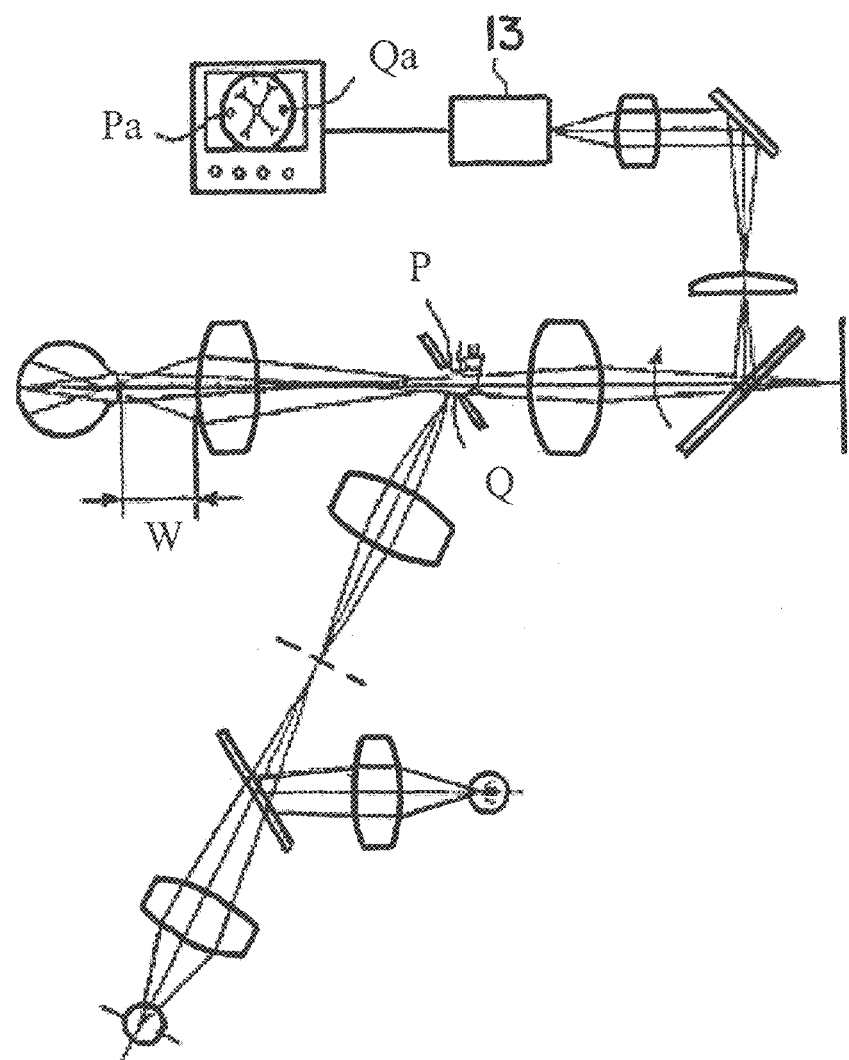
FIG. 17 (Prior-Art)

ALIGNMENT IMPROVEMENTS FOR OPHTHALMIC DIAGNOSTIC SYSTEMS

CROSS-REFERENCE TO RELATED APPLICATIONS

This application is a continuation and claims priority to U.S. application Ser. No. 17/082,714 filed on Oct. 28, 2020 entitled "ALIGNMENT IMPROVEMENTS FOR OPHTHALMIC DIAGNOSTIC SYSTEMS" (hereinafter the '714 Application). The '714 Application is a division of, and claims priority to, U.S. application Ser. No. 15/749,723, filed on Feb. 1, 2018, now U.S. Pat. No. 10,849,498 issued on Dec. 1, 2020, entitled "ALIGNMENT IMPROVEMENTS FOR OPHTHALMIC DIAGNOSTIC SYSTEMS," (hereinafter the '723 Application). The '723 Application is a U.S. National Phase Application under 35 U.S.C. § 371 and claims priority to PCT/EP201/069098 filed Aug. 11, 2016 entitled "ALIGNMENT IMPROVEMENTS FOR OPHTHALMIC DIAGNOSTIC SYSTEMS" (hereinafter the '098 Application). The '098 Application is an International Application and claims priority to U.S. Provisional Application Ser. No. 62/204,317 filed on Aug. 12, 2015 entitled "ALIGNMENT IMPROVEMENTS FOR OPHTHALMIC DIAGNOSTIC SYSTEMS" (hereinafter the '317 Application) The '714 Application, '723 Application, '098 Application and '317 Application are hereby incorporated by reference in their entirety for all purposes.

FIELD

The embodiments presented herein concern the addition of various feedback mechanisms including visual and audio feedback mechanisms to ophthalmic diagnostic systems for self-alignment of patients to these systems.

BACKGROUND

Correct alignment of the human eye to an ophthalmic diagnostic system is generally critical to performance. For example, correctly aligning the pupil of the eye to the pupil or aperture of the imaging system is critical for imaging the human retina, especially for white light fundus photography. Fundus photography is challenging compared to other forms of fundus imaging, such as confocal scanning ophthalmoscopy, because the pupil or aperture of the imaging system has a more complicated geometry and a larger total pupil aperture is desirable to take a clean image. Existing fundus cameras are usually operated by a technician who uses various feedback mechanisms and alignment aides to position the fundus camera, which is mounted on an adjustable mechanical stage, relative to a subject whose head is held in a fixed position by a rigid chinrest. Smaller portable or handheld fundus cameras are expertly positioned by the technician using additional hands, eyecups, stabilizing bars, and the like, to attempt to achieve repeatable positioning of the fundus camera to the subject's eye. Such lower cost portable fundus cameras often have a reduced set of alignment aids for the technician and therefore require a higher degree of skill to achieve a good photo. A large fraction of the cost of most fundus imaging devices goes towards the achievement of this alignment both in terms of mechanical placement of the imaging device relative to the eye, and alignment aides which help the operator or system know how to move to achieve best alignment.

Self-alignment, where a subject moves oneself, or the instrument, to achieve alignment between the two, is a requirement in some situations where no operator-technician is available, and may be a significant cost savings in other situations. To enable fundus cameras (or ophthalmic instruments in general) which can be aligned by the subject without technician assistance, it is desirable that the instrument have alignment aids to provide the subject with feedback to make the correct alignment modifications with minimum effort and training, and acquires a good measurement with high repeatability. Home care is set to become an increasingly important market as the need for 'aging in place' solutions increases; and as the cost of other components of diagnostic equipment, especially digital cameras and computational equipment, reduces. Home care presents a special case in which an auxiliary operator is less likely available to help acquire the fundus photo. In this case, the subject and instrument must work together to acquire the photo without dramatically adding to the cost of the device.

Existing fundus cameras commonly provide several forms of visual stimulus to the eye of a person whose retina is being imaged, which might be used to help a subject self-align to the fundus camera. Good alignment requires that 1) the pupil of the eye is positioned accurately in three dimensions relative to the illumination and collection pupils of the fundus camera, 2) the gaze of the eye is in the correct angular direction, and 3) the retina is in focus. Existing fundus cameras provide alignment relative to only the illumination pupil and does not inform about the alignment relative to a collection pupil.

Light from the illumination path of the fundus camera commonly illuminates the retina of the subject for the purpose of providing a retina preview to the operator before the documentation photograph flash. In some devices this light may be of low intensity white light, low intensity red light to which the human eye has relatively low sensitivity, or infrared light to which the eye has very low sensitivity. When a device is properly aligned, this light usually covers a region of the retina slightly wider than the field of view of the fundus camera. If this light is sufficiently bright, it visibly illuminates the illumination path exit pupil of the device from a range of angles similar to the field of view. When a subject approaches the fundus camera from a distance, the subject can visualize the illumination pupil of the camera as an illuminated virtual object, a few millimeters in diameter, apparently floating in space a few centimeters beyond the objective lens of the fundus camera. As the subject comes closer to correct alignment, looking into the fundus camera and moving his eye towards superimposition with the illuminated virtual object, it becomes impossible to focus on that virtual object, and the subject begins to see the shadow of his own eye pupil, as illuminated by the bright virtual object near his eye. This appears to the subject as a circularly illuminated field which increases in size as the subject approaches the correct axial location, and shifts in lateral position depending on the lateral alignment. When the subject successfully places his eye such that the illumination reaches a maximum field size and maximum brightness, the pupil of the eye is optimally aligned with respect to the illumination pupil of the fundus camera and most of the light is passing through uninhibited.

Fixation targets are commonly used in fundus cameras to orient the gaze direction of a subject to a particular direction. Frequently the fixation target is presented through the optics of the fundus camera to present to the same eye being imaged. The fixation target may be moved relative to the field of view of the fundus camera in order to guide the subject such that different portions of the retina are within the field of view of the fundus camera. Multiple images acquired with different fixation locations may be montaged together to form a mosaic covering a larger field of view than the fundus camera could collect in a single exposure. Such fixation targets are commonly presented such that they are in focus for the subject, and have at least some feature with small angular extent such that the subject may orient gaze direction with high precision. Some fixation targets may include a region of larger lateral extent, especially for individuals with low central vision, who may not be able to perceive a small target at the center of field. The subject may have access to a focus knob and control the position of lenses inside the system such that fixation focus is optimized, which may simultaneously focus the fundus camera sensor to achieve a focused photograph. In some fundus cameras (e.g. ZEISS Visucam), the fixation target may be projected back through the collection pupil. If this is the case, seeing the fixation target is enough to verify that at least some portion of the collection pupil is unobstructed.

FIG. 1 illustrates a series of vignetting and alignment conditions for a fundus imaging system based on a single illumination pupil. The left column 102 of the figure shows a series of frontal views of an eye pupil with illumination beam footprint superimposed. The middle column 104 shows a series of sagittal views of an eye with a pupil as aligned relative to an illuminating beam with an exit pupil located at the intersection of two chief rays. The right column 106 shows frontal views of the resulting illuminated area on the retina. Each row illustrates an alignment condition. In particular, the top row 108 illustrates the case of ideal alignment (as indicated by reference numeral 118). In this case, the exit pupil of the illumination is axially aligned such that it forms a small, focused footprint, centered on the eye pupil (as indicated by reference numeral 116); the retinal illumination covers a full field and is bright (as indicated by reference numeral 120). The second row 110 illustrates the case of lateral misalignment (as indicated by reference numeral 124). In this case, the exit pupil of the illumination is axially aligned such that it forms a small, focused footprint, off-center on the eye pupil (as indicated by reference numeral 122); the retinal illumination covers a full field and is dim (as indicated by reference numeral 126). The third row 112 illustrates the case where the eye is too close to the optical instrument and is laterally misaligned (as indicated by reference numeral 130). In this case, the exit pupil of the illumination is axially aligned such that it forms a larger, defocused footprint, off-center on the eye pupil (as indicated by reference numeral 128) and the retinal illumination covers a partial field where rays corning in from angles above are attenuated (as indicated by reference numeral 132). The bottom row 114 illustrates a situation where an eye is too far from the optical instrument and is laterally misaligned (as indicated by reference numeral 136). In this case, the exit pupil of the illumination is axially aligned such that it forms a larger, defocused footprint, off-center on the eye pupil (as indicated by reference numeral 134) and the retinal illumination covers a partial field where rays corning in from angles below are attenuated (as indicated by reference numeral 138).

According to the Gullstrand principle, to avoid the brightest reflex, that of the corneal reflection, the illumination beam must be separated in the corneal plane from the collection beam. To avoid reflection from the lens surfaces and scattering by lens opacities, the beams must also be separated in their trajectory through the lens. In general it is desirable to spatially separate the illumination pupil and collection pupil. One common way to achieve this separation is with a ring aperture for illumination (201) and a central aperture for collection (202) as illustrated in FIG. 2A. The left portion 210 of this figure shows a frontal view of an iris and pupil with a superimposed ring aperture 201 for illumination and a central disk aperture 202 for collection. The middle portion 212 of the figure displays the illumination envelope for the top and bottom of the ring aperture showing that the center of the cornea and lens are not illuminated. The right portion 214 of the figure shows the resulting, relatively wide, illumination footprint on the retina. Sometimes this ring (201) is broken such that it appears as a dashed ring, as may be needed to physically implement an approximation to the ring. An alternative arrangement to achieve separation of illumination and collection pathways is to employ two separated pupils, for example two distinct circular apertures side by side as illustrated in FIG. 2B. The left portion 216 of this figure shows side by side disk apertures for illumination (203) and collection (204). The center portion 218 of this figure shows that the illumination envelope is offset to one side in the eye pupil for this separation arrangement. The right portion 220 of this figure shows that a smaller retinal field can be illuminated while maintaining the Gullstrand constraints when using side by side disk apertures. The ring aperture is relatively expensive to implement, but has the advantage that a wider field can be illuminated with greater uniformity and less beam overlap in the anterior segment than the side by side aperture configuration.

A fundus photograph will record a vignetted field that is the intersection of the vignetted fields of the illumination and the collection. A clear field of view must exist for both the illumination and the collection in order to obtain an unvignetted final image. Because the fixation target has a limited lateral extent, it tests the vignetting only over a relatively small field, typically in the region of the macula. Fundus cameras that illuminate the retina with a ring aperture and use a central circular aperture for collection will experience significant vignetting of the illumination beam before any vignetting of the collection beam is possible. The ring shaped aperture may make it difficult to notice small amounts of vignetting of the field, in particular when the eye is too close to the fundus camera objective. In this case, small amounts of occlusion of the illumination aperture will dim the central field rather than produce a more obvious shadow on the peripheral field. Unwanted illumination of the iris may cause observable flare in the photograph if this very bright light finds a beam path back to the detector. On the other hand, with side by side illumination and collection pupils, it is likely that an alignment optimized by attempting to observe an unvignetted illumination field while simultaneously observing a fixation target, will occlude a portion of the collection pupil, and vignette the collection field, however the fixation target will appear normal.

SUMMARY

The present application describes the addition of feedback mechanisms to ophthalmic diagnostic devices to assist a person/subject to align himself/herself to a device. The feedback mechanisms utilize visual stimulus to the eye of the subject. The ability to perform self-alignment to a fundus camera is of primary interest for very low cost, and or portable fundus camera implementations. The feedback allows the subject to know that their eye is correctly located in angle and position within tolerance for an acceptable image.

An ophthalmic diagnostic device may use visual and non-visual (e.g., audio) feedback mechanisms independently or in combination with one another. The device may provide a means for a user to provide feedback to the device to confirm that an alignment condition has been met. Alternatively, the device may have a means for sensing when acceptable alignment has been achieved. The device may capture diagnostic information during the alignment process or may capture after the alignment condition has been met.

According to one aspect of the subject matter described in the present application, a device for imaging the retina of a subject's eye includes a source for illuminating the subject's eye; an illumination path from the source to the subject's eye, said illumination path having an illumination aperture; a collection path for light reflected from the subject's eye, said collection path having a collection aperture; optics for projecting a visual stimulus through each of the illumination aperture and the collection aperture to the retina of the subject's eye for aiding the subject to self-align the eye to the device; a means for identifying when an acceptable alignment has been achieved; a detector for collecting light returning from the subject's eye and generating signals in response thereto; and a processor for generating an image of the subject's eye from the signals collected when the acceptable alignment has been achieved.

The above aspect may additionally include one or more of the following features. For instance, the features include: that the illumination aperture and the collection aperture are spatially separated; that the visual stimulus relative to each of the illumination and the collection aperture are distinguishable via different 1) colors, 2) brightness, 3) shapes, and 4) temporal modulation; and that a series of fixation points are projected along with the visual stimulus, the fixation points being projected depending on a desired gaze direction of the subject.

The device according to the above aspect is particularly advantageous over the existing devices in a number of respects. By way of example and not limitation, (1) the device achieves optimal or acceptable alignment relative to both the illumination and the collection pupils with a certain tolerance limit, (2) provides a fixation point combined with a clear field border projected through the collection pupil of the device while simultaneously providing a low level illumination over the full field of view (FOV) through the illumination aperture of the device, (3) provides an image of the pupil superimposed with a view of the illumination and collection apertures that may be formed purely optically without the aid of additional sensors or pixel displays.

According to another aspect of the subject matter described in the present application, a device for imaging the retina of a subject's eye includes a source for illuminating the subject's eye; a detector for receiving light reflected from the eye in response to the illumination; a position measurement system to determine a position of the subject's eye relative to one or more planes; a signal generator to generate an audible feedback in response to the determined position; an audible signal transducer to project the audible feedback to the subject's ears for aiding the subject to self-align the eye to the device; and a processor for generating an image of the subject's eye when an acceptable alignment has been achieved.

The above aspect may additionally include one or more of the following features. For instance, the features include: that the audible feedback is a feedback using one or more tones; that the feedback using one or more tones includes 1) a first pitch tone to indicate an alignment that is too close, 2) a second pitch tone that is different from the first pitch tone to indicate an alignment that is too far, and 3) a third pitch tone that is different from the first and the second pitch tones to indicate a perfect alignment; that a feedback tone is presented simultaneously with a reference tone to correct alignment; that the audible feedback is a feedback using a sound localization stimulus in which an apparent direction of a sound indicates a direction the subject should move to achieve the acceptable alignment; and that the audible feedback is a feedback using synthetic speech.

According to yet another aspect of the subject matter described in the present application, a device for imaging the retina of a subject's eye includes a source for illuminating the subject's eye; an illumination path from the source to the subject's eye, said illumination path having an illumination aperture; a collection path for light reflected from the subject's eye, said collection path having a collection aperture; optics for projecting a visual stimulus through an aperture larger than the illumination aperture or collection aperture to the retina of the subject's eye for aiding the subject to self-align the eye to the device; a means for identifying when an acceptable alignment has been achieved; a detector for collecting light returning from the subject's eye and generating signals in response thereto; and a processor for generating an image of the subject's eye from the signals collected when the acceptable alignment has been achieved.

The above aspect may additionally include one or more of the following features. For instance, the features include: that the visual stimulus includes a representation of an actual eye position of the subject relative to an ideal alignment position indicator, said ideal position alignment indicator indicating to the subject a desired gaze direction; that the representation of the actual eye position is an image of the iris of the subject; and that a position coded alignment message is transmitted to the retina of the subject's eye when a location containing the position coded alignment message overlaps with the subject's pupil.

The device according to the above aspect is particularly advantageous over the existing devices in a number of respects. By way of example and not limitation, (1) the device projects a visual stimulus similar to traditional alignment aids to the subject's retina via an active display. For example, projecting preview images of the retina, or alternatively projecting an image of pupil or alignment snowballs. These alignment feedbacks are projected such that viewing them does not disturb, or assists with gaze alignment, (2) provides a parallax based 'gunsight' with two targets placed at or imaged to different apparent distances from the subject, with additional cues for depth or alignment tolerance, and (3) illuminates positions outside the correctly aligned pupil with regions projecting alignment messages indicating where the subject should move the instrument or his/her eye.

It should be noted that while the above aspects/embodiments are described with respect to a white light fundus camera in mind, these embodiments may be adapted to other ophthalmic devices such as scanning based fundus imaging system, optical coherence tomography (OCT) systems, therapeutic lasers, air puff tonometers, wavefront analyzers, corneal topographers, retinal scanning security devices, etc.

The embodiments described herein are not all-inclusive and many additional embodiments will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIGS. 3A and 3B illustrate two prior art fundus imaging system designs. In particular, FIG. 3A illustrates an external illumination design. FIG. 3B illustrates an internal illumination design.

FIG. 17 illustrates a prior-art fundus camera system that is modifiable by one embodiment of the present invention to aid in self-alignment.

DETAILED DESCRIPTION

All patent and non-patent references cited within this specification are herein incorporated by reference in their entirety to the same extent as if the disclosure of each individual patent and non-patient reference was specifically and individually indicated to be incorporated by reference in its entirety.

FIGS. 3A and 3B illustrate elements of two typical prior art fundus imaging systems (see for example, DeHoog, E. and J. Schwiegerling (2009). "Fundus camera systems: a comparative analysis." *Appl. Opt.* 48(2): 221-228). It should be understood that the fundus imaging systems of FIGS. 3A and 3B are just two exemplary systems that can be used with the various embodiments discussed in the present application. However, this is not limiting and other ophthalmic diagnostic/imaging systems are also possible for use with these embodiments and are within the scope of the present disclosure.

Figure 1:
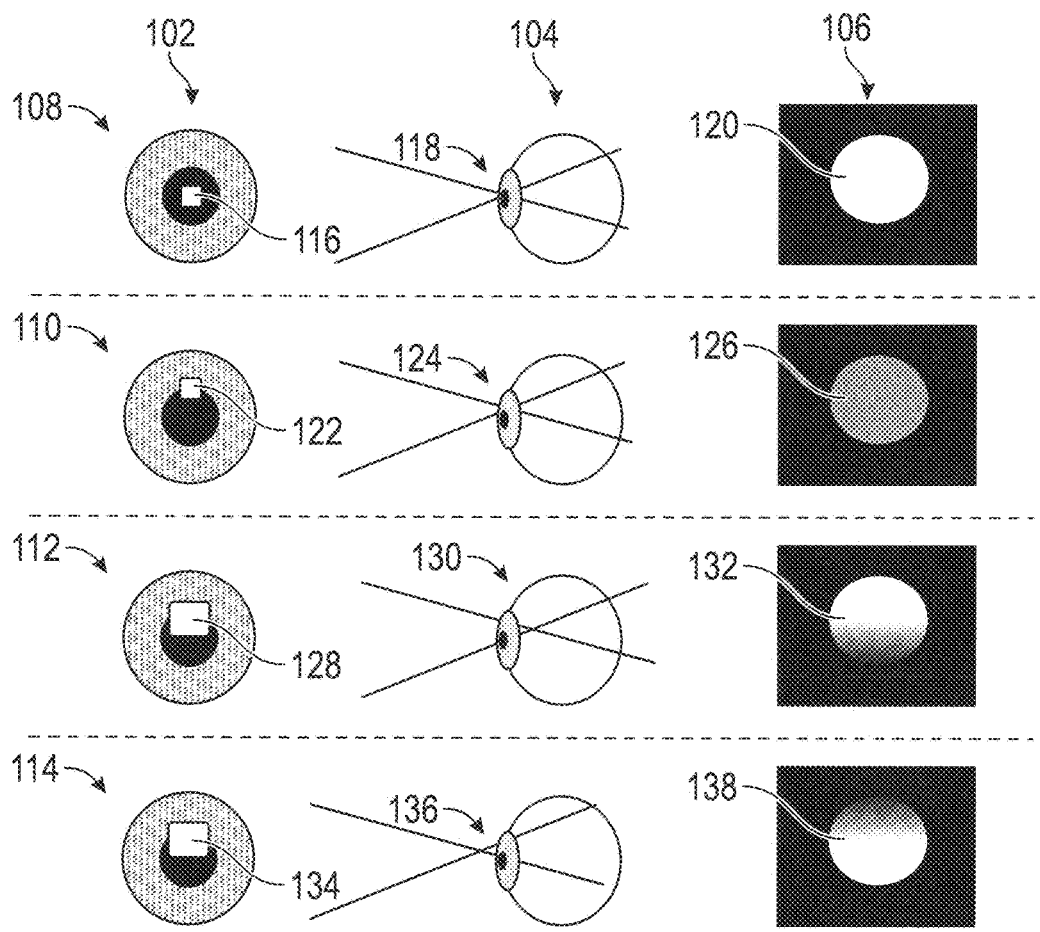
FIG. 1 illustrates exemplary cases of vignetting and alignment based on a single illumination pupil.
Figure 2A:
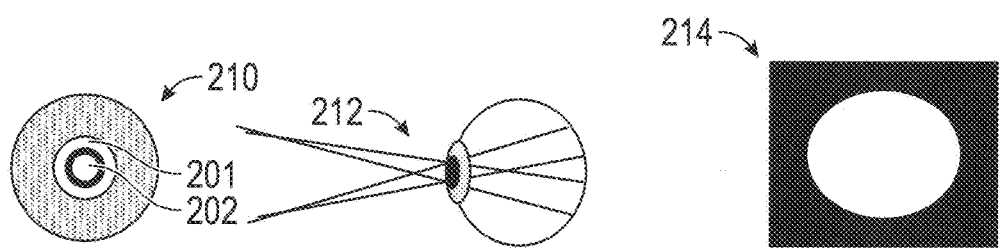
FIGS. 2A and 2B illustrate two exemplary ways of separating an illumination beam from a collection beam.
Figure 2B:
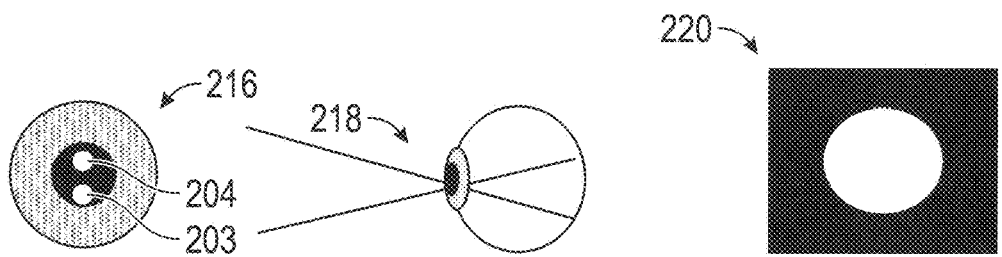

FIG. 3A illustrates an external illumination design 300 using a beam splitter (302) placed in front of the eye (301) to combine the illumination and imaging paths. A source (308) is imaged onto the pupil of the eye by lenses (305) and (307). An annulus (306) is placed between the lenses and positioned conjugate to the pupil of the eye. FIG. 3B illustrates an internal illumination design 310 that uses a mirror with a central hole (312) placed conjugate to the pupil of eye (301) to combine the illumination and imaging paths. In FIG. 3B, the fact that the illumination and imaging paths share the objective lens (314) requires a more complicated system to eliminate back reflections. The source (316) is reimaged to the mirror by lenses 318, 320, and 322. Back reflections from the front and back surfaces of the objective are removed by a black dot (324) placed conjugate to the back surface of the objective. The internal system 310 of FIG. 3B uses a single aspheric objective (314) to reduce the number of surfaces contributing to the back reflections, whereas the objective (303) in the external system 300 of FIG. 3A can consist of multiple elements because it is not part of the illumination pathway and will not contribute to back reflections. The only difference in the imaging paths of both systems is the existence of a baffle (304) in FIG. 3A. This baffle, placed conjugate to the pupil of the eye, helps reduce corneal back reflections and limits the entrance pupil diameter of the imaging system. In the internal system 310, the mirror with the central hole (312) serves the same purpose as the baffle (304) in the external system 300. An iris can be placed immediately behind the mirror with the central hole to allow for further control of the entrance pupil diameter and for elimination of back reflections. The above description describes systems 300 and 310 that implement pupil splitting similar to FIG. 2A while U.S. Pat. No. 6,409,341 describes a retina illumination system implementing pupil splitting similar to FIG. 2B.

Figure 4:
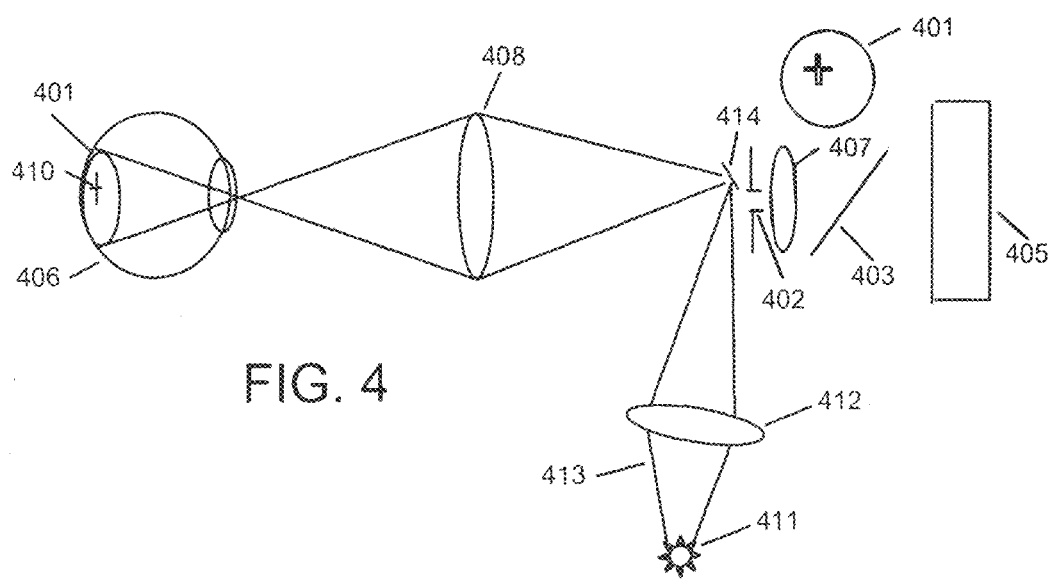
FIG. 4 illustrates one exemplary embodiment of a visual feedback mechanism for self-alignment where an indicator that identifies if the full extent of the collection field of view (FOV) is unvignetted is supplied to a subject being imaged.

In one embodiment of a visual feedback mechanism that can be used with an ophthalmic imaging system including, but not limited to those illustrated in FIGS. 3A and 3B, an indicator that identifies if the full extent of the collection field of view (FOV) is unvignetted, is supplied to the subject being imaged. One example of such an approach is illustrated in FIG. 4. A source (411) produces a beam of light to illuminate the illumination path (413) and optics (412) projects a pattern identifying the edge of the field of view (401) (also referred to herein as the FOV indicator) through an illumination aperture mirror (414) and an objective lens (408) to appear on the retina of the subject's eye 406. The FOV indicator (401) of the fundus camera sensor (405) may be projected back via a focusing lens (407) through the collection aperture (402) to appear on the retina of the subject (406). To project the FOV indicator back through the collection aperture (402), it is advantageously inserted to the optical path after this aperture on the detection path, preferably near an image plane conjugate to the retina. It may be added as a separated optical path with a beamsplitter (403). This beamsplitter may be a non-polarizing beamsplitter with a low reflectivity so as to minimally affect the light collection of the fundus camera. Alternatively, a polarizing beamsplitter might be used, in particular if the optical design of the fundus camera already requires a polarizing element in the collection path. Alternatively, a flip-in mirror may be used.

Figure 5:
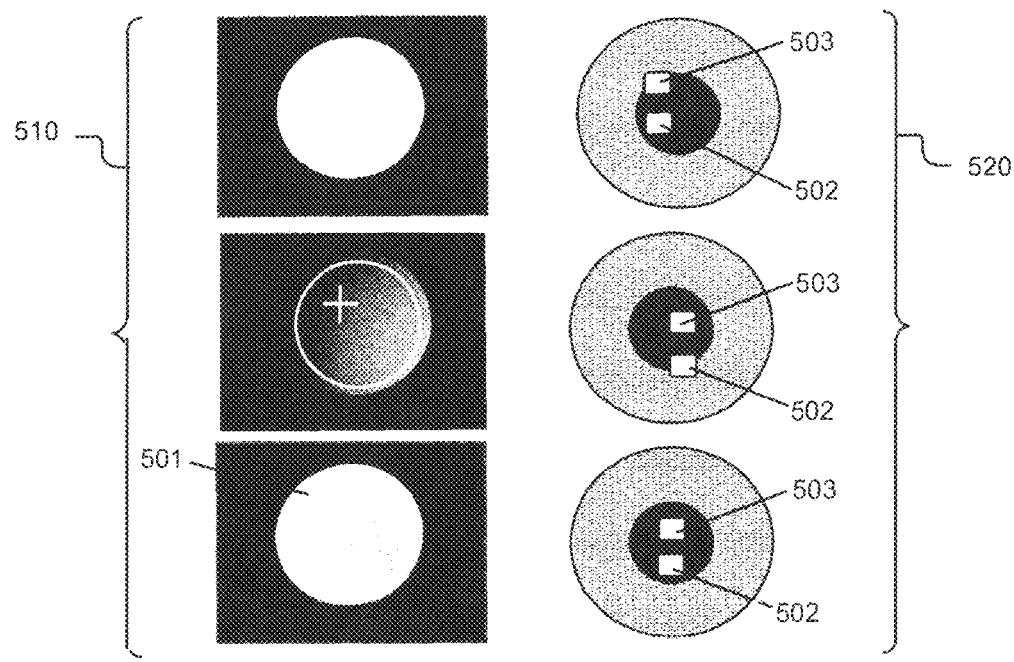
FIG. 5 illustrates exemplary images observed by the subject's eye and corresponding frontal views of the subject's eye pupil according to the embodiment of FIG. 4.

In some instances, the FOV indicator (i.e., the pattern identifying the edge of the field of view) may take the form of a solid or broken ring of illumination (501) as illustrated in FIG. 5. The left hand column 510 of FIG. 5 illustrates the view observed by the subject with the imaged eye corresponding to alignment conditions described in the right hand column 520. The right hand column 520 provides a view of the iris of the subject's imaged eye in relation to the illumination aperture (502) and collection aperture (503). If the full ring is observable to the subject, and of expected brightness, the collection pupil is unobstructed by the iris of the eye. This FOV indicator also provides a spatial reference to know the area which should be filled with the illumination path. It is important that the subject is able to distinguish the FOV indicator when superimposed on top of the low level illumination from the illumination path. The FOV indicator may be projected in a different color, and/or greater brightness than the low level illumination. Whereas the illumination path projects a diffuse light over a wide field, it is advantageous if the FOV indicator provides a distinct line to be easily differentiated. Alternatively, the indicator from the illumination path, in order to expose the retina to less light prior to photo, may project only a ring border, differentiated from the collection path by color or other feature.

Figure 6:
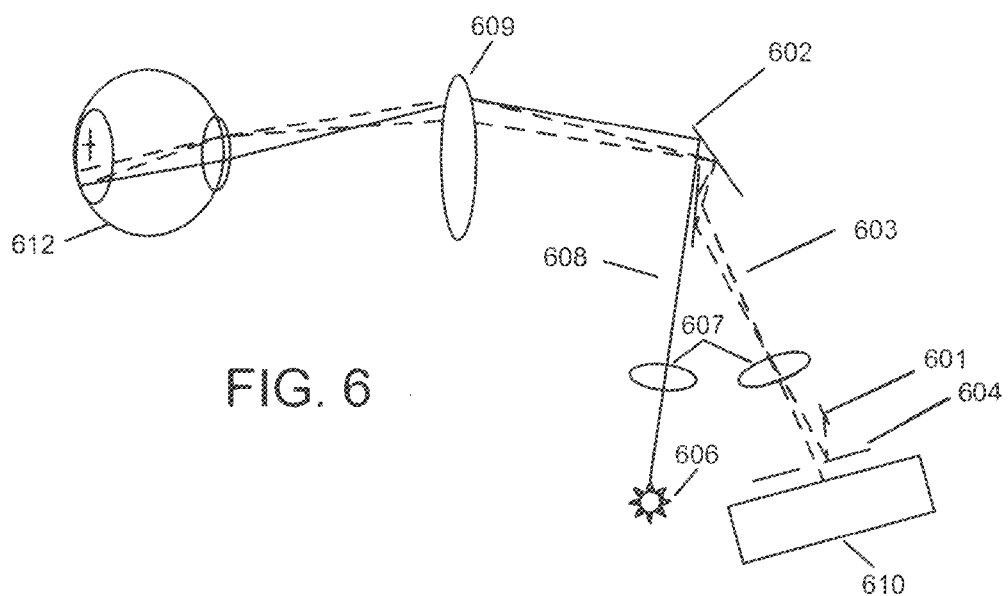
FIG. 6 illustrates an alternate embodiment of the visual feedback mechanism discussed in FIG. 4.

In fundus camera systems where the collection field is scanned, for example by a scanning element such a variable angle mirror (602) as is illustrated in FIG. 6 (see for example, U.S. Pat. No. 4,732,466 and Zeiss' Cirrus HD-OCT), the projected FOV indicator (601) may be separated from the collection path (603) spatially by an aperture stop (604) at a location where the retinal image is scanned (601), and any offset in position compensated by an offset in timing of stimulus presentation. Similar to FIG. 4, reference numeral 606 represents the source for illuminating the eye 612; 607 represents optics for projecting the FOV indicator in the illumination path 608 and collection path 603; 609 represents the objective lens; and 610 represents the fundus camera sensor.

The FOV indicator may be implemented in common with a fixation target (e.g., see FOV indicator 401 containing the fixation target 410 in FIG. 4), or independently. In the case where the FOV indicator is implemented in common with the fixation target, it is desirable that the FOV indicator is representative of the recorded field, and is therefore usually static with respect to the optical axis of the instrument. It may be desirable to adjust the fixation position to alternate positions to cause the gaze direction of the eye to change. The fixation may be directed to positions inside or outside of the field of view of the fundus camera. Both the FOV indicator and the fixation target may be implemented as illuminated pixels in a display providing continuous variability of fixation position. Alternatively, the fixation may be selected from a finite selection of positions as distinct LED positions, which illuminate masked regions on a sparsely populated circuit board (see for example, FIG. 7).

Alternatively, a static ring may be illuminated and the position of an LED may be moved around by motors or manually. In fundus camera systems where the collection field is scanned, such as the line scanning ophthalmoscope in the ZEISS Cirrus HD OCT, the projected illumination may consist of a one-dimensional array of illuminators where the sequencing of illumination is coordinated with the scanning of the collection field. It may be desirable to implement the fixation entirely independent from the FOV indicator. For example, it may be desirable to implement fixation with an external binocular fixation light to implement fixation far off axis, while it is still desirable to project the FOV indicator through the collection pupil.

Figure 7:
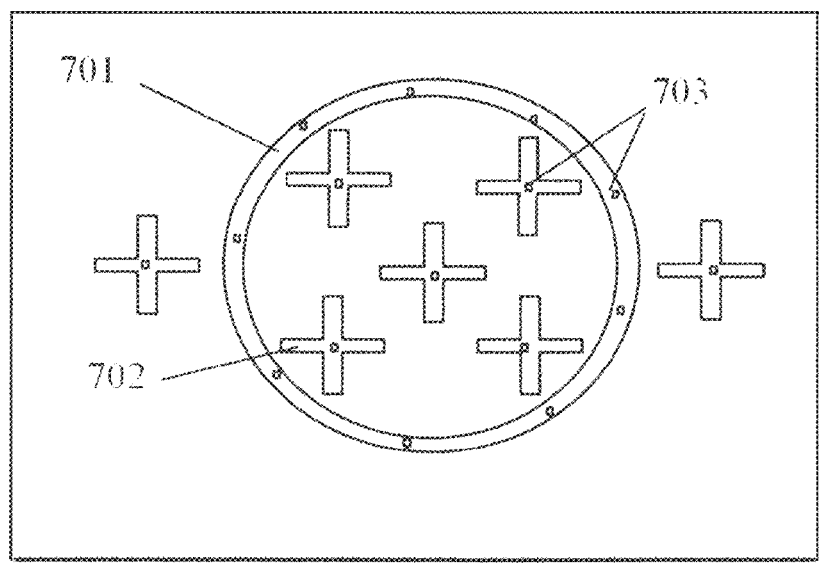
FIG. 7 illustrates a pattern of illuminators for variable direction fixation and a FOV indicator.

FIG. 7 illustrates a pattern of illuminators for variable direction fixation and a FOV indicator. The FOV indicator, represented by the ring 701, is fixed in position relative to the optical axis. Fixation points, represented by the cross shapes 702 are selectively illuminated depending on the gaze direction desired. Such a pattern may be created as a mask with predefined shapes at fixed locations where selection is performed by selectively illuminating LEDs (703) within each desired mask shape. Alternatively, the illuminated regions could be created by addressing pixels on a matrix type display.

Typically, for any feedback mechanism, a subject/patient must be somewhat aligned to the device in order to begin the finer alignments steps. A disadvantage of mechanisms which project feedback stimulus through the illumination and collection pupils of the device is that the alignment must already be rather good in order to transmit the feedback messages to the subject. This problem is particularly severe when the subject is well aligned in the axial dimension and the illumination and collection pupils are well focused and compact, in the plane of the subject's iris. For this reason, it is desirable to explore feedback mechanisms where the alignment message can be projected back to the subject through an aperture that is larger than either the illumination or collection pupils.

An iris camera that relays an image of the iris to an instrument operator is a commonly used method to position an ophthalmic device relative to an eye of a subject. In a second embodiment of a visual feedback mechanism according to the present application, this method may be adapted to self-alignment by providing the correct optics to receive light from the iris and relay it such that an image of the iris is focused on a retina of the person being imaged. One way to achieve this is to set up a fundus camera with an iris camera where the display screen is positioned such that the iris image can be observed with the fellow eye. The image from an iris camera may also be presented with a display projection system and inserted either into the illumination or collection path of the instrument. In the above cases, the image of the iris may be placed on the display at a location corresponding to the fixation location so that monitoring the pupil does not interfere with, but rather aides in directing the gaze of the subject. Additional information about the position of the illumination and collection pupils may be superimposed upon the iris image for position reference.

Figure 8:
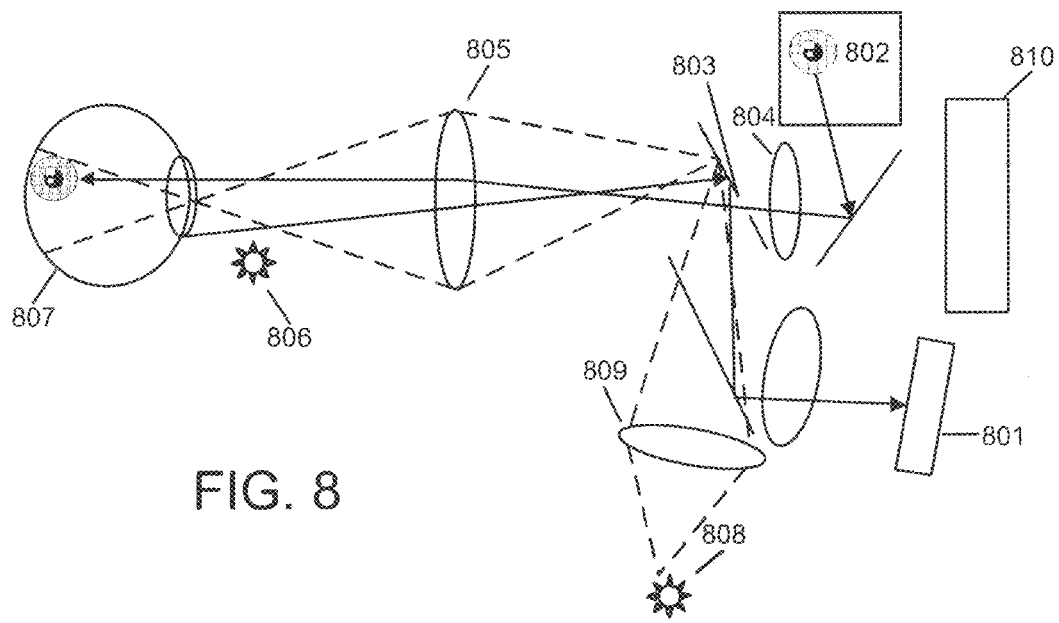
FIG. 8 illustrates another exemplary embodiment of a visual feedback mechanism for self-alignment where an iris camera is implemented in the illumination path of a fundus imaging system to record a position of the eye pupil.
Figure 9:
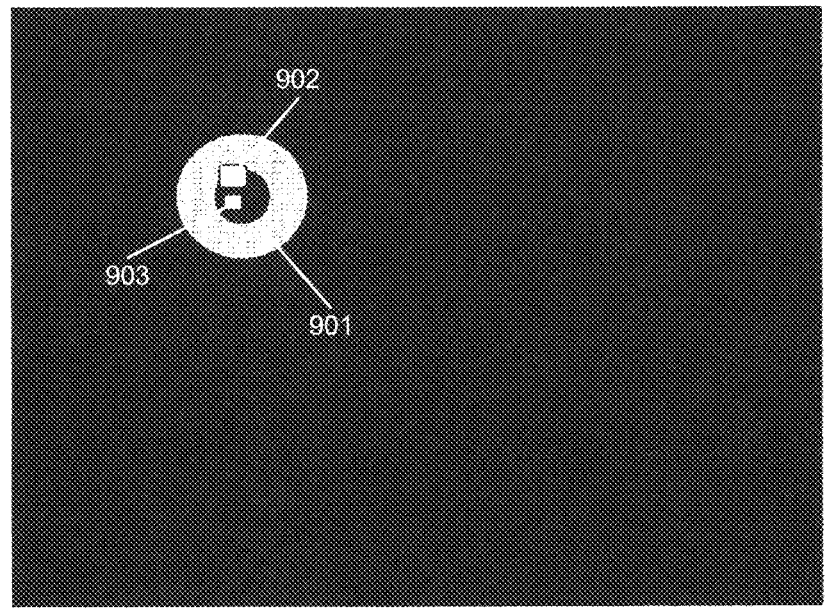
FIG. 9 illustrates an exemplary frontal view of the subject's eye pupil according to the embodiment of FIG. 8.

FIG. 8 shows an embodiment where an iris camera (801) is implemented in the illumination path of a fundus imaging system to record the position of the eye pupil, generate a display of the iris (802) in response thereto, and provide the display of the iris (802) projected through the lens (804) and the aperture of the collection path (803) to appear on the subject's eye (807). Here, reference numeral 805 represents the objective lens; 806 represents a source for illuminating the anterior portion of the eye 807; 808 represents an illumination source; 809 represents a lens used in illumination; and 810 represents the camera sensor. FIG. 9 illustrates details of the projected display inserted in the collection path. Computer generated alignment fiducials can be marked on the displayed image to indicate the locations of the system illumination pupil (903) and collection pupil (902) at the desired location of gaze fixation for the subject being tested. The iris image (901) is projected behind the computer generated apertures. Alignment is achieved when the computer generated apertures appear contained within the boundaries of the iris. The illumination and collection pupils need not be identified as physical apertures distinct from each other, but do identify a region that should be contained within the iris of the eye.

An all-optical iris position feedback may be alternatively delivered to the eye. An all optical system is advantageous in that it has a potential for low cost, high sensitivity to the human eye, and no electronic lag. Additional information about the position of the illumination and collection pupils may also be superimposed optically upon the iris image as described below. An upright image indicating the position of the illumination and collection pupils and the subject's superimposed iris should be presented in the direction of desired gaze.

Figure 10:
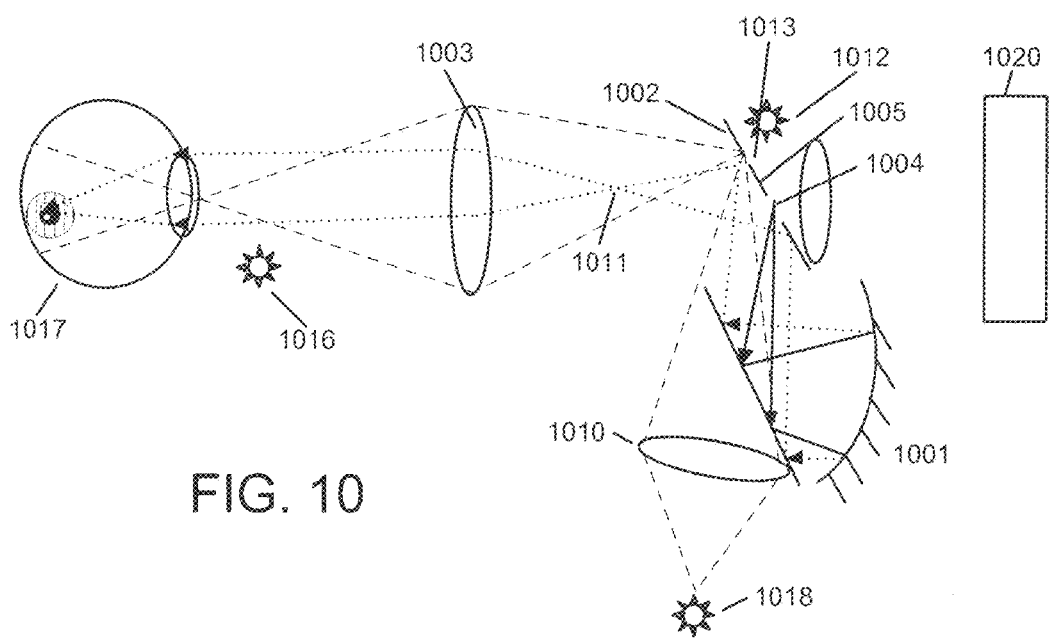
FIG. 10 illustrates another exemplary embodiment of a visual feedback mechanism where iris reflection is implemented in the illumination path with passive optics.
Figure 11:
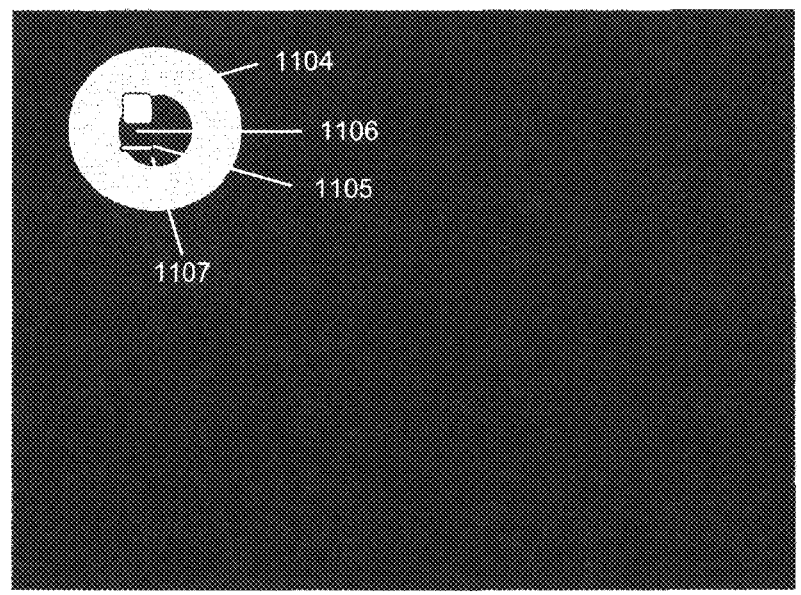
FIG. 11 illustrates an exemplary frontal view of the subject's eye pupil according to the embodiment of FIG. 10.

FIG. 10 shows an embodiment where the iris reflection is implemented in the illumination path of a fundus imaging system. One or more optical components represented by a concave mirror (1001), reflects light back such that the aperture mirror (1002) is imaged at a retinal conjugate (1011), which, for the system as drawn, lies at the back focal length of the objective (1003) for an emmetropic subject. Back illumination (1012) of the collection aperture (1004) and a fiducial aperture (1013) above the reflective portion of the aperture mirror corresponding to the illumination aperture (1005) provide visual references of the location of the illumination and collection aperture, to which the subject attempts to align the pupil of his own iris. Rays have been added to the diagram to clarify the imaging arrangement. Rays originating at the backlight (1012) and passing through the apertures in the aperture mirror (1002) towards the imaging system (1001) are represented by solid lines with arrowheads in the direction of light propagation. Rays returning from the concave mirror (1001) towards an inverted image of the aperture mirror located at the retinal conjugate (1011) are shown dashed with arrowheads in the direction of light propagation. A tilt may be introduced in the iris reflection path to shift the image of the illumination and collection pupils and iris towards a desired direction of gaze location away from the optical axis. As discussed elsewhere herein, reference numeral 1016 represents a source for illuminating the anterior portion of the eye 1017; 1018 represents an illumination source; 1010 represents a lens used in illumination; and 1020 represents the camera sensor. FIG. 11 shows the corresponding view presented to the eye of subject being imaged. The back illuminated apertures are shown at the position desired for fixation. When the subject is appropriately aligned, the illuminated collection pupil (1104) and the dark region (1106), bordered by the fiducial aperture bordering the opposite side of the illumination aperture (1105), should be contained within the image of the iris aperture (1107).

It is desirable that the subject should see their own iris in focus when their eye is correctly located in the axial direction, regardless of the refractive error of the particular subject. The goal of the self-aligning subject will be to place the iris into a plane which is optically conjugate to the illumination and collection apertures. The axial position of the mirror (1001) should first be adjusted such that the back illuminated apertures are best focused for the subject, thus compensating for the subject's refractive error. The subject should then adjust the position of his own eye such that the iris appears in focus at the same time as the back illuminated apertures.

It is desirable that the image of the iris be located at the direction of desired fixation such that monitoring the position of the iris simultaneously achieves the goal of fixation. A tilt may be introduced in the optical path to achieve an image of the iris which appears off-axis relative to the optical axis of the fundus camera. This tilt may be introduced by a physical tilt or translation of a reflective surface or by a translation of a refractive surface which is equivalent to inserting a wedge into the optical path.

Parallax is a displacement or difference in the apparent position of an object viewed along two different lines of sight. As described in U.S. Pat. No. 5,474,548, when two targets are placed at different distances along a line, a subject may precisely define both the gaze direction and the lateral position of the eye by attempting to move the eye such that the targets appear to be superimposed. This alignment system is quite familiar as the "iron sight" which defines the position of a shooter's eye relative to the barrel of a gun.

In a further embodiment of a visual feedback mechanism for self-alignment, a parallax based "gunsight" is described for fundus imaging. If the eye must be placed such that it meets the alignment condition for a plurality of defined lines, the eye may be located axially as well as laterally. 'Perfect' alignment is unnecessary and any attempt to achieve perfect alignment may actually exhaust a subject and degrade performance. It is preferable to identify when alignment is good enough, or within an acceptable tolerance between the instrument pupils and the edge of the human iris.

A target consisting of two shapes at different distances, where a first shape at one distance consists of an inner and an outer border, and a set of features on a second shape at the other distance lies in between the inner and outer border, can provide axial and lateral alignment with an indication of alignment tolerance. One of the targets is ideally optically in the same plane as the fundus camera sensor, such that when the subject is focused on the target, he/she is simultaneously focused on the fundus camera sensor. This target may be illuminated with a relatively large pupil such that the subject has a precise ability to determine focus. The other target, which must be placed in an out of focus plane, is preferably illuminated with a small pupil such that the subject is not disturbed by its fuzzy appearance and does not attempt to focus on it.

Figure 12:
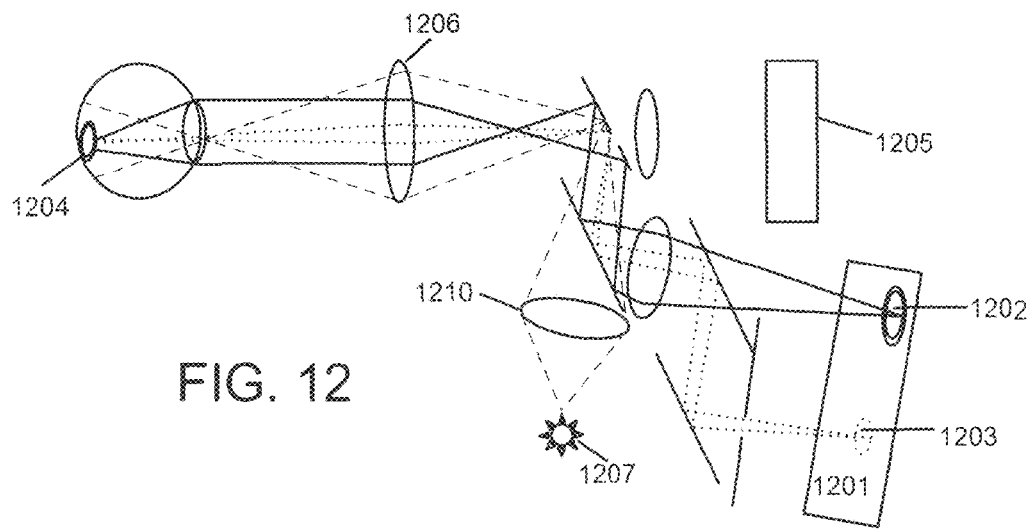
FIG. 12 illustrates another exemplary embodiment of a visual feedback mechanism for self-alignment based on a parallex based "gunsight" procedure for fundus imaging.
Figure 13:
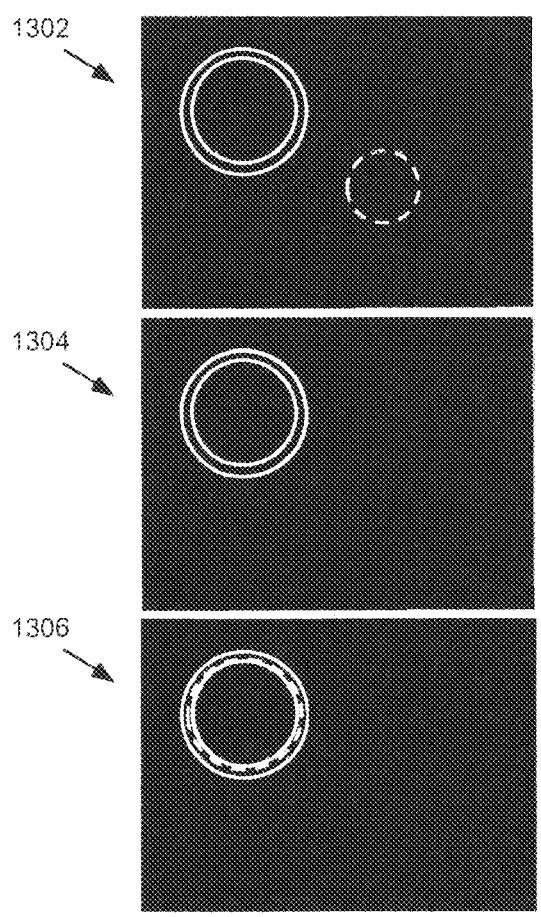
FIG. 13 illustrates exemplary images observed by a subject's eye for self-alignment within a certain tolerance according to the embodiment of FIG. 12.

FIG. 12 illustrates an embodiment of a parallax based alignment target. A pixel display (1201) in the illumination path creates targets at two different optical depths. One target (1202) is projected with a large numerical aperture, and is in the same optical plane as the fundus camera sensor (1205). The other target (1203), which must be defocused relative to the retina (1204), is projected with a small numerical aperture such that defocus does not cause significant blurring on the retina (1204). Here, reference numeral 1206 represents the objective lens, reference numeral 1207 represents the illumination source, and reference numeral 1210 represents the illumination lens. FIG. 13 illustrates one embodiment of a parallax based alignment target as displayed to the subject. The top panel 1302 shows the two targets misaligned both laterally (as indicated by the lateral displacement of the targets) and axially (as indicated by their mismatched size). The middle panel 1304 shows the two targets aligned laterally but misaligned axially. The bottom panel 1306 shows the targets aligned within tolerance in both dimensions.

Figure 14:
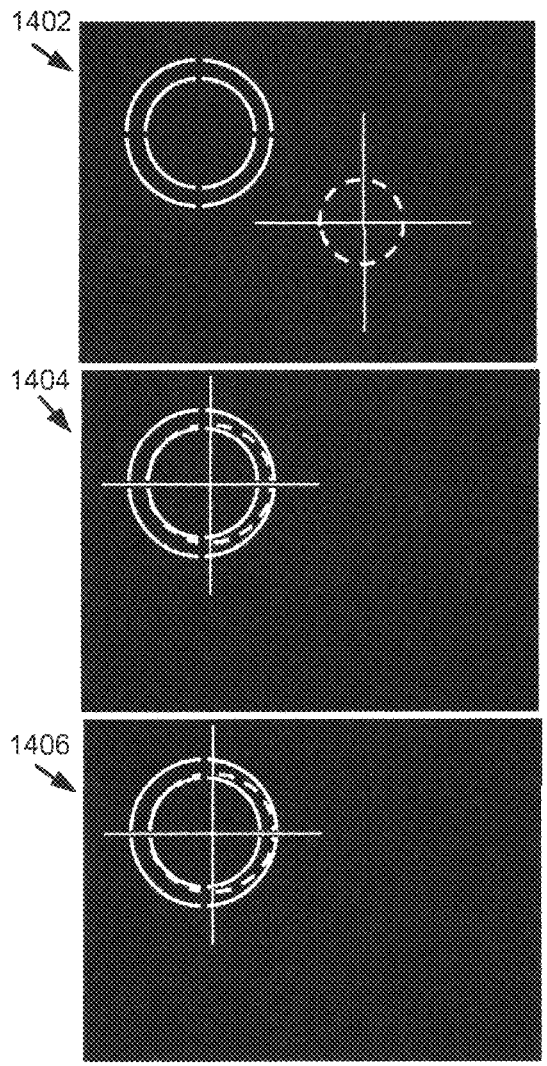
FIG. 14 illustrates another exemplary images observed by the subject's eye for self-alignment within a certain tolerance according to the embodiment of FIG. 12.

The precision of alignment tolerance in the axial and lateral directions can be adjusted with some independence by changing the optical distance between the two targets and by changing the separation between the inner and outer border. Alternatively, the geometry of the shapes can be specific to indicate different tolerances on lateral alignment vs. axial distance. In general, to achieve tighter tolerance axially, it is necessary to use larger field angles for the same separation of tolerance bands. To achieve tighter tolerance laterally one can make a smaller spacing between tolerance bounding regions. It is more straightforward to make a target with tight lateral tolerance and loose axial tolerance than with tight axial tolerance and loose lateral tolerance. FIG. 14 illustrates an embodiment of a parallax based alignment target having smaller tolerances in the lateral direction than in the axial direction. The top panel 1402 shows the targets misaligned both laterally and axially. The middle panel 1404 shows the targets aligned within tolerance axially but misaligned laterally. The bottom panel 1406 of FIG. 14 shows the targets aligned within tolerance for both dimensions.

Figure 15:
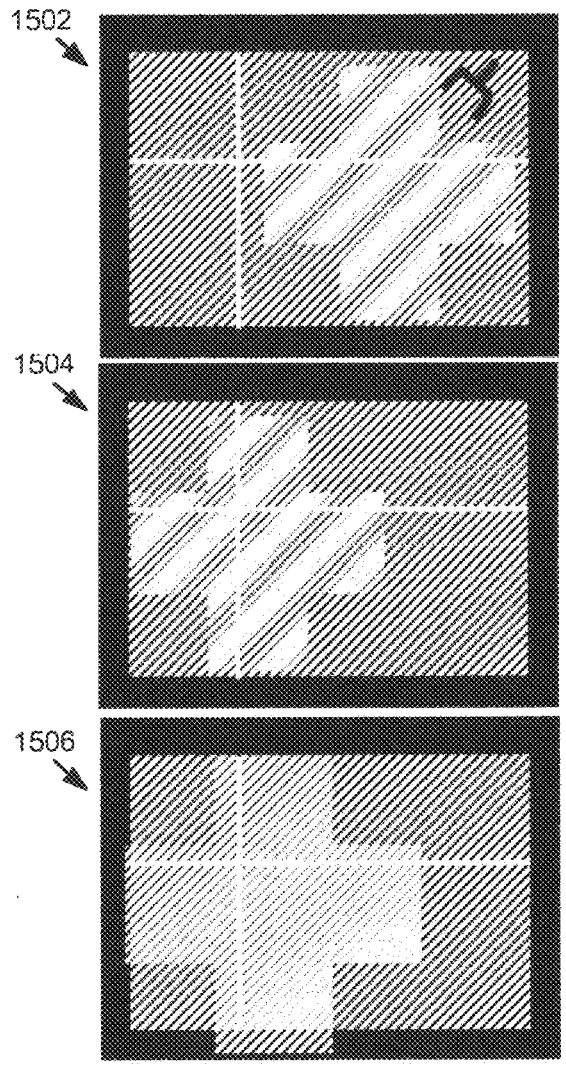
FIG. 15 illustrates an embodiment of a parallax based alignment with the use of Moiré patterns to achieve tight tolerance on axial position and loose tolerance on lateral position.

In an alternative embodiment of a parallax based alignment aid, two grid patterns may be superimposed to create a Moiré pattern where the apparent modulation frequency indicates the difference in apparent pattern spatial frequency and thus can be a rather sensitive indicator of axial distance. Tolerance may be indicated for example where the Moiré pattern shows more than two cycles over the spatial extent of the interfering area. FIG. 15 illustrates an embodiment of a parallax based alignment target illustrating the use of Moiré patterns to achieve tight tolerance on axial position with loose tolerance on lateral position. The top panel 1502 shows the pattern misaligned laterally and axially. The heavy brace mark superimposed on the top panel of the figure indicates one cycle of the Moiré pattern. The middle panel 1504 shows the pattern aligned within tolerance laterally but misaligned axially. The bottom panel 1506 shows the target aligned in both dimensions within tolerance.

Figure 16A:
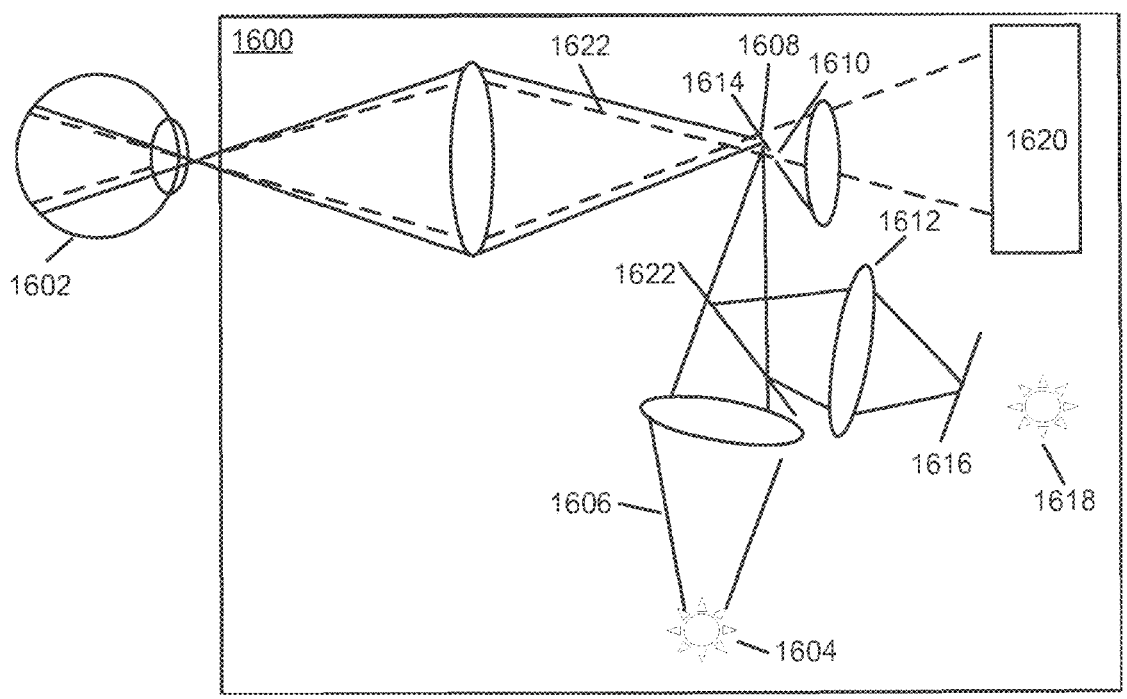
FIG. 16A illustrates another exemplary embodiment of a visual feedback mechanism for self-alignment where locations of an ophthalmic imaging instrument exit pupil plane are coded with alignment messages and are projected to a subject's eye.

In another embodiment of a visual feedback mechanism that allows for self-alignment of an ophthalmic imaging system, locations of the instrument exit pupil plane are coded with messages which appear on the retina of the subject only when that portion of the pupil plane is aligned such that its message passes through the pupil of the eye. Such an alignment message could indicate that a specific alignment condition is met, or that a particular corrective action should be taken. For example, if the eye is aligned too low relative to the device, an image projected through a lower portion of the pupil plane may project an arrow indicating to the subject that they should move their head up relative to the device. Such messages could be implemented in multiple directions around the illumination and collection pupils. Small portions of the pupil plane are individually coded with a different alignment message. A simple way to create such a coded pupil is to place a diffractive optical element (such as the ones created by Avago Digital Optics) or a phase hologram, at a plane conjugate to the illumination and collection pupils. FIG. 16A illustrates one such embodiment. In particular, FIG. 16 illustrates an ophthalmic diagnostic device 1600 to measure a subject's eye 1602. As depicted, the device 1600 includes a source 1604 for illuminating the subject's eye 1602; an illumination path 1606 from the source 1604 to the subject's eye 1602, the illumination path 1606 having an illumination aperture 1608; a collection path 1622 for light reflected from the subject's eye, the collection path having a collection aperture 1610; optics 1612 for projecting a visual stimulus through an aperture 1614 that is larger than the illumination aperture or collection aperture to the retina of the subject's eye 1602 for aiding the subject to self-align the eye to the device; a holographic diffractive element 1616 placed conjugate to the pupil plane and back illuminated by a light source 1618; and a detector/camera sensor 1620 for collecting light returning from the subject's eye and generating signals in response thereto. The aperture 1614 that is larger than the illumination aperture or collection aperture may be realized by a relatively large annular mirror surface where the collection aperture 1610 passes through the hole in the mirror, and the illumination aperture 1608 reflects off a relatively small portion of the mirror. The optics 1612 for projecting the visual stimulus can be implemented as a branch of the illumination path separated by a partially reflective beamsplitter 1622.

The far-field diffraction pattern of an illuminated segment will be projected on the retina if the light from that portion of the pupil plane is transmitted through the pupil of the eye. The fundus illumination and collection portions of the pupil plane may be left clear or may have diffractive patterns or lenslets introduced to optimize imaging quality, without communicating a specific alignment message. For example, the illumination pupil may be coded with a diffuser to achieve better illumination uniformity, while the collection pupil may be coded with a trefoil, or other types of aberration phase plates to achieve wavefront coding as described by Eva Acosta (see for example Acosta, E., Arines, J., Hernandez, R., Grewe, A., and Sinzinger, S. (2014). Wavefront coding implementation for retinal imaging systems. Invest. Ophthalmol. Vis. Sci. 55, 1586-1586, hereby incorporated by reference). Diffractive optic pattern generators usually work best when illuminated with a narrow wavelength band and high spatial coherence. Alternatively, these messages may be created via alternate imaging paths for different portions of the pupil plane and masks containing different alignment messages for each coded portion of the pupil plane. Depending on the size of the eye pupil, multiple alignment coded apertures may be transmitted to the subject's retina simultaneously. It may be desirable that the messages presented to the subject can be interpreted in a consistent way if multiple apertures are simultaneously illuminated. Two recommended patterns are arrows projecting in a direction of desired motion, such that arrows in opposite direction may cancel, or a circle which fully circumscribes the FOV when alignment condition is met.

Figure 16B:
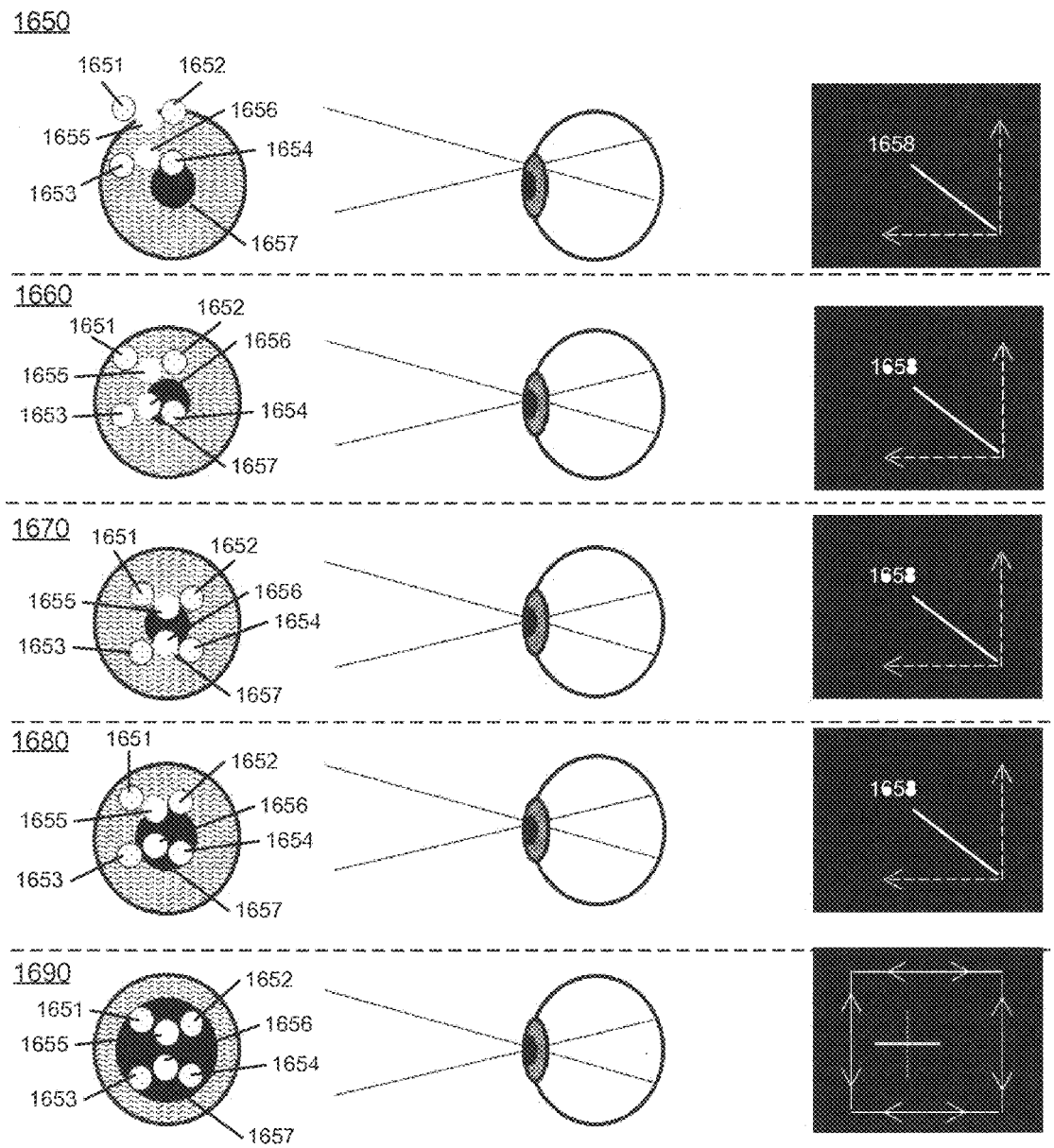
FIG. 16B illustrates a series of scenarios where different position coded alignment messages are projected to a subject's retina dependent on alignment and pupil size of the subject's eye.

FIG. 16B illustrates a series of scenarios where different position coded alignment messages are projected to the retina dependent on alignment and pupil size of the eye. The messages are encoded in spatially defined apertures which are projected as 'message coding locations' to the same plane as the illumination and collection pupils. When the location containing an alignment message overlaps with the pupil of the eye, the message encoded in that position is transmitted to the retina. Locations (1651, 1652, 1653, and 1654) around the illumination pupil (1655) and collection pupil (1656) are coded with different messages. Fixation targets are projected through either the illumination pupil or the collection pupil, depending on the design. In this example, the message coding locations are symmetrical about the center of the illumination/collection pupils. The total image projected on the retina is the superposition of all messages transmitted through the eye pupil (1657). In the top panel 1650 of FIG. 16, the eye pupil (1657) is aligned so that it partially overlaps with only one message coding location (1654) such that the corresponding message (1658) is transmitted with partial intensity, and the pupil through which the fixation target is communicated (either 1655 or 1656) does not overlap with the pupil of the eye (1657) therefore the fixation target is not transmitted. The dashed arrow indicates that the alignment message is transmitted with partial intensity. In the second row 1660, the eye pupil (1657) is aligned such that the message 1654 is fully transmitted and the fixation target (1659) is also transmitted. In the third row 1670, optimal alignment for a small eye pupil (1657) is illustrated. Here the fixation target is transmitted through one of the illumination/collection pupils (1655 or 1656), however because of the small eye pupil size, none of the alignment messages are transmitted. In the fourth row 1680, message 1654 is fully transmitted while messages 1652 and 1653 are unequally transmitted. The messages partially cancel logically and the remaining alignment message is still transmitted to the subject along with the fixation target. The fifth row 1690 illustrates optimal alignment for a large pupil 1657. Here the messages from all message coding locations (i.e., 1651, 1652, 1653, and 1654) are fully transmitted and no improvement in the alignment is logically suggested to the user.

FIG. 17 illustrates a prior art fundus camera system, which can be modified according to another embodiment of a visual feedback mechanism to aid in self-alignment, as discussed below. One traditional alignment aid used in fundus cameras consists of point sources (P and Q) such that their image lies at approximately the exit pupil of the device. When these images coincide with the pupil of the eye, they are located such that the light reflected from the cornea is collimated and passes through the collection pupil of the fundus camera. Two spots (snowballs) (Pa and Qa) are observed nearly focused on the fundus camera sensor (13). In another embodiment of a visual feedback mechanism to aid in self-alignment of ophthalmic imaging systems, feedback such as this may be projected through a display as described earlier, preferably referenced to a fixation target direction such that monitoring the position and focus of the fixation spots simultaneously achieves gaze orientation, and does not distract from it. Alternatively, an all optical implementation may be achieved by arranging optics such that a corneal reflection from a set of point sources or from another illumination is reflected back to the eye in a manner that is readily interpreted by a subject.

Figure 18A:
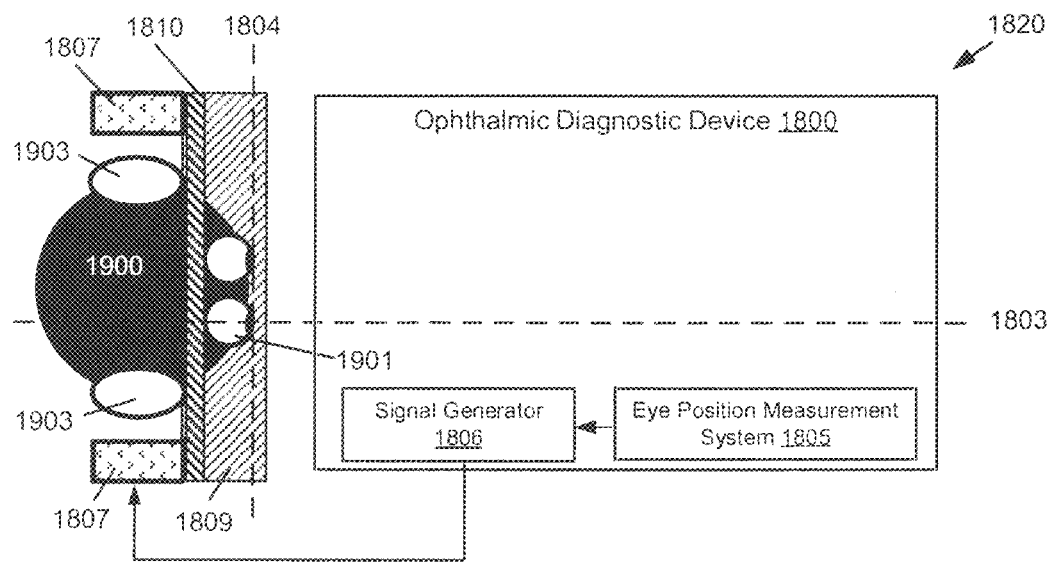
FIGS. 18A and 18B, respectively, illustrate a top view and a side view of an ophthalmic diagnostic device (1800) that is configured to deliver an audible feedback to a patient (1900) for self-alignment.
Figure 18B:
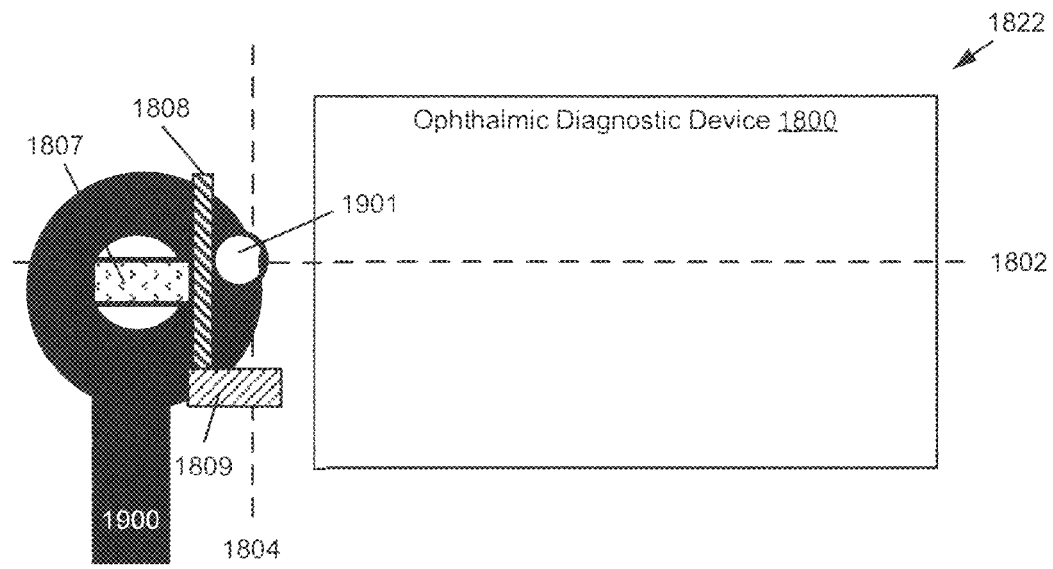

FIGS. 18A and 18B, respectively, illustrate a top view (1820) and a side view (1822) of an ophthalmic diagnostic device (1800) that is configured to deliver an audible feedback to a subject (1900) for self-alignment. An eye (1901) of the subject needs to be measured. The ophthalmic device (1800) has a position to which the subject should align the eye defined in vertical (1802), horizontal (1803), and axial (1804) planes relative to the optics of the device. The device contains eye position measurement system (1805) to determine the position of the subject's eye relative to the one or more planes (e.g., 1802, 1803, and/or 1804), a signal generator (1806) to generate an audible feedback signal in response to the measured position, and one or more transducers (1807) to project the audible signal to one or both ears (1903) of the subject. The transducers may optionally be mounted (1808) to maintain a position relative to chinrest (1809) and forehead rest (1810).

The eye position measurement system (1805) may be an anterior segment camera well known in the art to determine the position of the anterior segment of the eye relative to the ophthalmic diagnostic device (see for example, U.S. Pat. Nos. 7,331,670, 7,445,336, 7,364,295, and 7,641,340). Usually the output of such a component will be a digital or analog argument indicating the position of the subject relative to an ideal reference position. The signal generator (1806) translates the relative position argument into a waveform that, when transduced to create audible sound vibrations, can be interpreted as instructions to the subject. One way to convert the positional information to a usable instruction is to match the positional information to a look-up table of recorded instructions. For example, if the positional information indicates that the axial position is negative relative to axial reference plane, the message "move back a little" might be replayed to the subject. Verbal instructions are limited because 1) they have language dependencies and 2) the length of messages have bandwidth limitations, which make communication too slow. A feedback using tones can give nearly instantaneous feedback. For example, a specific pitch may indicate a perfect alignment, a high pitch may indicate an alignment too near, and a low pitch may indicate an alignment too far. Using three well separated tones may be sufficient for a digital distinction of "too close", "too far", and "within tolerance". A more continuous feedback can be delivered if the feedback tone is presented simultaneously with a reference tone. The beat frequency of the feedback tone with the tuning reference can indicate to the subject how large of a correction is needed (see for example, Winckel, Fritz (1967). *Music, Sound and Sensation: A Modern Exposition*, p.134). For example, if the reference frequency is set equal to the frequency of the feedback at ideal alignment, a beat frequency that is very low indicates the best alignment. Musical theory can be used to achieve an intuitive emotional response to correct alignment, for example by setting the ideal offset between the feedback frequency and reference frequency (or superimposed frequencies) to create, for example a major chord when superimposed (see for example, Benward & Saker (2003). *Music: In Theory and Practice*, Vol. I, p. 67&359. Seventh Edition). In this way, the subject feels to be tuning a musical instrument to 'a happy place' when positioning the head to the correct location. Sound localization, the perception of which is due to phase differences between the sound received by the left and right ears and "head related transfer functions" can be used to simulate sound coming from a specific position relative to the listener (see for example, Middlebrooks, John C., and David M. Green. "Sound localization by human listeners." *Annual review of psychology* 42.1 (1991): 135-159). The sound can 'feel' to be coming from virtually any angle including in front, to the side, above, below, or behind a listener. Such binaural audio stimulus can be used to indicate instructions in multiple axis more intuitively. For example, the directionality of the feedback tone may indicate the direction along which the subject should shift the head for proper alignment. For binaural playback instructions to be properly received, the transducers (1807) should be positioned at fixed positions relative to the subject's ears (1903), and each should stimulate only one ear, a task for which traditional earphones are ideal.

Figure 19:
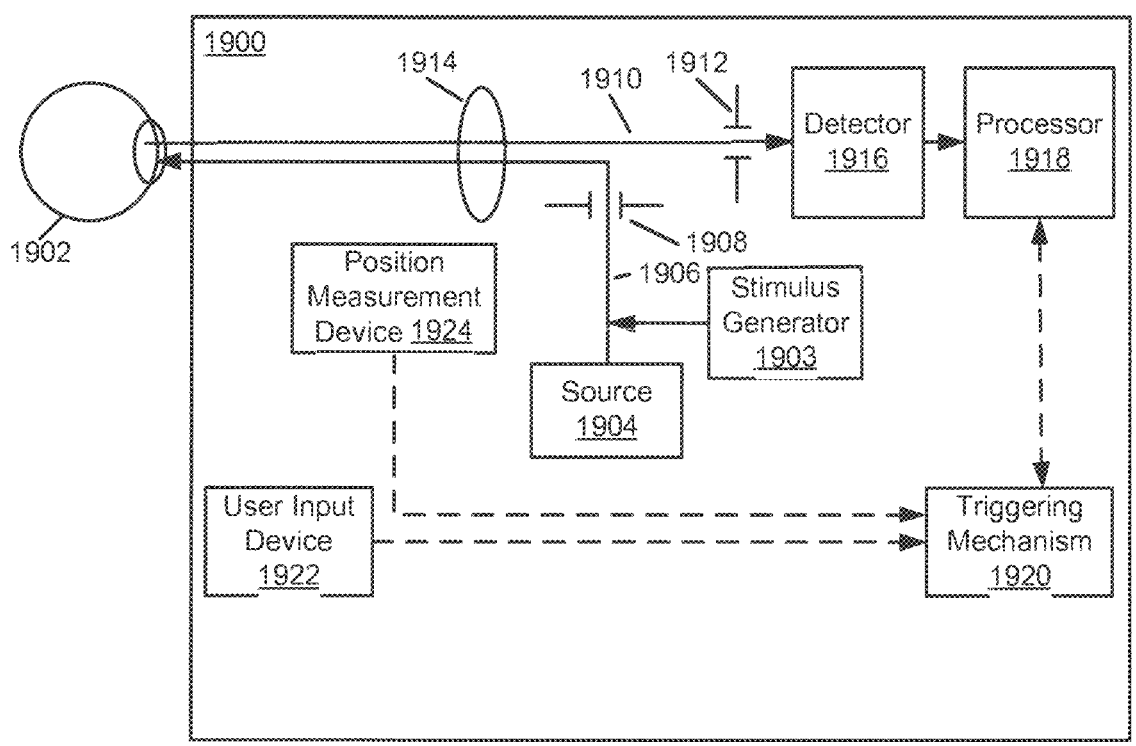
FIG. 19 illustrates a general ophthalmic device for imaging the retina of a subject's eye.

FIG. 19 illustrates a general ophthalmic instrument/device 1900 for imaging the retina of a subject's eye 1902. As depicted, the device 1900 includes a source 1904 for illuminating the subject's eye 1902; a stimulus generator 1903 for generating a visual stimulus; an illumination path 1906 from the source 1904 to the subject's eye 1902, the illumination path having an illumination aperture 1908; a collection path 1910 for light reflected from the subject's eye 1902, the collection path 1910 having a collection aperture 1912; optics 1914 for projecting a visual stimulus through each of the illumination aperture 1908 and the collection aperture 1912 to the retina of the subject's eye 1902 for aiding the subject to self-align to the device 1900; a detector

1916 for collecting light returning from the subject's eye and generating signals in response thereto; a processor 1918 for generating an image of the subject's eye 1902 from the signals; and a triggering mechanism 1920 for determining when an acceptable alignment has been achieved. The determination of the acceptable alignment may be used to trigger a photographic flash, or indicate to the subject that sufficient data has been collected and the subject may relax.

In some instances, the processor 1918, in cooperation with the triggering mechanism 1920, determines that an acceptable alignment condition has been achieved when the subject's pupil is aligned with the illumination aperture 1908 and the collection aperture 1912 within a certain tolerance limit. This determination or sensing may be achieved using an IR preview beam. In some instances, the processor 1918 and the triggering mechanism 1920 may be coupled together as a single unit to perform the functionalities discussed herein with respect to each. The device 1900 may optionally include a user input device 1922 that is operable by the subject to indicate, in cooperation with the triggering mechanism 1920, to the processor 1918 when a full field of view of the projected visual stimulus is observable by the subject with an expected brightness. The user input device 1922 may be implemented as a mechanical clicker, a button, or a voice command receiver for the subject to provide feedback to the device 1900 to confirm that an acceptable alignment has been achieved. In some instances, user input device 1922 and the triggering mechanism 1920 may be coupled together as a single unit to perform the functionalities discussed herein with respect to each. The device 1900 may further optionally include a position measurement device 1924 for measuring the position of the anterior segment of the eye 1902, which is then input to the triggering mechanism 1920 for determining whether an acceptable alignment has been achieved. In some instances, the device 1900 may capture diagnostic information during the alignment process or may capture the information after an acceptable alignment has been achieved.

For all embodiments described herein, the ophthalmic instrument/device may be relatively immobile and the subject moves his/her eye to meet the relatively static instrument pupil, similar to a desktop microscope. The instrument may have controls which the subject may manipulate to align the instrument pupil towards the pupil of his/her own eye, similar to a traditional fundus camera. Alternatively, the instrument may be a handheld device which the subject moves into place and controls position with his/her hands, similar to a pair of binoculars or a spyglass. As previously mentioned, the instrument may include a chin rest and/or forehead rest to support the patient relative to the instrument. Alternatively, the device could have one or more eyecups that come in contact with the subject and surround the subject's eye(s). Such an eye cup could be a permanent part of the instrument or could be a disposable component. The eye cup could contain additional sensors that are operably connected to the processor.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

The invention claimed is:

1. A device for imaging a retina of a subject's eye, the device comprising:
   an illumination source for illuminating the subject's eye;
   an illumination path from the illumination source to the subject's eye,
   the illumination path having an illumination aperture;
   a collection path for light reflected from the subject's eye to a detector,
   the detector collecting light returning from the subject's eye and generating signals in response thereto,
   the collection path having a collection aperture different from the illumination aperture;
   optics for projecting a visual stimulus, through a projection aperture, the visual stimulus surrounding the illumination aperture and the collection aperture to the retina of the subject's eye,
   the projected visual stimulus providing alignment information;
   an alignment identifier for identifying an acceptable alignment; and
   a processor for generating an image of the retina of the subject's eye, from select-signals generated by the detector, the select signals corresponding to light collected from the acceptable alignment;
   wherein the visual stimulus includes a representation of an actual eye position of the subject's eye relative to an ideal alignment position indicator.

2. The device as recited in claim 1, wherein the representation of the actual eye position is an image of the iris of the subject's eye.

3. The device as recited in claim 2, further comprising:
   a camera for recording the image of the iris; and
   a display for presenting the image of the iris.

4. The device as recited in claim 1, further comprising passive optics for relaying to the subject, the representation of the actual eye position relative to the ideal alignment position indicator.

5. The device as recited in claim 1, wherein the visual stimulus includes a plurality of position coded alignment messages positioned around the illumination aperture and the collection aperture.

6. The device as recited in claim 1, wherein the device is one of a fundus camera, an optical coherence tomography (OCT) system, or a scanning based retinal imager.

7. A device for imaging a retina of a subject's eye, the device comprising:
   an illumination source for illuminating the subject's eye;
   an illumination path from the illumination source to the subject's eye,
   the illumination path having an illumination aperture;

a pixel display in the illumination path for projecting a first visual target at a first optical depth and a second visual target at a second optical depth to the subject's eye, wherein the first visual target is projected with a first numerical aperture and is placed in an in-focus plane, and wherein the second visual target is projected with a second numerical aperture smaller than the first numerical aperture and is placed in an out-of-focus plane;

a collection path for light reflected from the subject's eye to a detector, the detector collecting light returning from the subject's eye and generating signals in response thereto, the collection path having a collection aperture different from the illumination aperture;

optics for projecting a visual stimulus, through a projection aperture, the visual stimulus surrounding the illumination aperture and the collection aperture to the retina of the subject's eye, the projected visual stimulus providing alignment information;

an alignment identifier for identifying an acceptable alignment; and a processor for generating an image of the retina of the subject's eye, from select-signals generated by the detector, the select signals corresponding to light collected from the acceptable alignment.

8. The device as recited in claim 7, wherein the processor is further configured to act as the alignment identifier by determining when the first visual target and the second visual target are aligned both laterally and axially within predefined lateral and axial tolerance limits.

9. The device as recited in claim 8, wherein Moiré patterns are used to achieve the predefined axial tolerance limit along the axial direction.

10. The device as recited in claim 7, wherein the visual stimulus includes a plurality of position coded alignment messages positioned around the illumination aperture and the collection aperture.

11. The device as recited in claim 7, wherein the device is one of a fundus camera, an optical coherence tomography (OCT) system, or a scanning based retinal imager.

12. A device for imaging a retina of a subject's eye, the device comprising:

an illumination source for illuminating the subject's eye;

an illumination path from the illumination source to the subject's eye, the illumination path having an illumination aperture;

a collection path for light reflected from the subject's eye to a detector, the detector collecting light returning from the subject's eye and generating signals in response thereto, the collection path having a collection aperture different from the illumination aperture;

optics for projecting a visual stimulus, through a projection aperture, the visual stimulus surrounding the illumination aperture and the collection aperture to the retina of the subject's eye, the projected visual stimulus providing alignment information;

a diffractive optical element, located at a plane conjugate to the illumination aperture and the collection aperture, for creating a set of position coded alignment messages, in the projected visual stimulus, that are projected to the retina of the subject's eye, each position coded alignment message indicating a direction where the subject's eye should move to achieve a desired alignment;

an alignment identifier for identifying an acceptable alignment; and a processor for generating an image of the retina of the subject's eye, from select-signals generated by the detector, the select signals corresponding to light collected from the acceptable alignment.

13. The device as recited in claim 12, wherein the diffractive optical element is a phase hologram.

14. The device as recited in claim 12, wherein the visual stimulus includes a plurality of position coded alignment messages positioned around the illumination aperture and the collection aperture.

15. The device as recited in claim 12, wherein the device is one of a fundus camera, an optical coherence tomography (OCT) system, or a scanning based retinal imager.

* * * * *